(12) United States Patent
Baba et al.

(10) Patent No.: US 8,303,507 B2
(45) Date of Patent: Nov. 6, 2012

(54) ULTRASONIC DOPPLER DIAGNOSTIC APPARATUS AND MEASURING METHOD OF DIAGNOSTIC PARAMETER

(75) Inventors: Tatsuro Baba, Otawara (JP); Hiroyuki Tsujino, Irvine, CA (US); Kazuya Akaki, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1836 days.

(21) Appl. No.: 11/219,753

(22) Filed: Sep. 7, 2005

(65) Prior Publication Data

US 2006/0052704 A1 Mar. 9, 2006

(30) Foreign Application Priority Data

Sep. 7, 2004 (JP) ................. 2004-260156

(51) Int. Cl.
*A61B 8/00* (2006.01)
(52) U.S. Cl. ........... 600/453; 600/454; 600/455; 702/66
(58) Field of Classification Search .................. 600/456, 600/454, 438
See application file for complete search history.

(56) References Cited

U.S. PATENT DOCUMENTS

| | | | |
|---|---|---|---|
| 5,287,753 A | 2/1994 | Routh et al. | |
| 5,515,857 A | 5/1996 | Tsujino et al. | |
| 5,628,321 A | 5/1997 | Scheib et al. | |
| 5,634,456 A * | 6/1997 | Perrone | 124/76 |
| 5,634,465 A | 6/1997 | Schmiesing et al. | |
| 5,647,366 A | 7/1997 | Weng | |
| 5,935,074 A | 8/1999 | Mo et al. | |
| 6,050,948 A * | 4/2000 | Sasaki et al. | 600/453 |
| 6,920,349 B2 * | 7/2005 | Schreck | 600/512 |

FOREIGN PATENT DOCUMENTS

| | | |
|---|---|---|
| JP | 7-241290 A | 9/1995 |
| JP | 9-322897 A | 12/1997 |
| JP | 11-146880 A | 6/1999 |
| JP | 2003-284718 | 10/2003 |

(Continued)

OTHER PUBLICATIONS

Huang et al. "Time-frequency spectral analysis of heart rate variability during induction of general anesthesia". British Journal of Anesthesia. vol. 79: 754-758. 1997.*

(Continued)

*Primary Examiner* — Long V. Le
*Assistant Examiner* — Helene Bor
(74) *Attorney, Agent, or Firm* — Oblon, Spivak, McClelland, Maier & Neustadt, L.L.P.

(57) ABSTRACT

A Doppler signal detecting unit 42 and spectrum calculating unit 44 measure a Doppler spectrum from a reception signal obtained by ultrasonic wave transmission/reception with respect to a diagnosis region of an object to be examined. A local maximum/minimum detecting unit 62 detects a plurality of local maximum/minimum pairs with respect to a trace waveform generated by a trace waveform generating unit 61 on the basis of the Doppler spectrum. A feature amount selecting unit 64 selects a desired waveform from a plurality of local maximum/minimum pairs in a predetermined cardiac cycle set by a cardiac cycle setting unit 63 by using heartbeat information from a living body measuring unit 9 on the basis of a preset selection criterion. A diagnostic parameter is measured on the basis of the position information or amplitude information of the selected waveform.

30 Claims, 25 Drawing Sheets

FOREIGN PATENT DOCUMENTS

JP    2004-222754 A    8/2004

OTHER PUBLICATIONS

U.S. Appl. No. 12/327,190, filed Dec. 3, 2008, Baba, et al.
U.S. Appl. No. 12/140,607, filed Jun. 17, 2008, Baba, et al.
A. Cimponeriu, et al., "A Theoretical Analysis of Acute Ischemia and Infarction Using ECG Reconstruction on a 2-D Model of Myocardium", IEEE Transactions on Biomedical Engineering, vol. 48, No. 1, Jan. 2001, pp. 41-54.
U.S. Appl. No. 12/238,829, filed Sep. 26, 2008, Baba, et al.
U.S. Appl. No. 12/824,696, filed Jun. 28, 2010, Baba.
Japanese Office Action issued Jan. 25, 2011, in Patent Application No. 2005-259677 (with English Translation).
K. Tei, "2. Ultrasonic Diagnosis of Heart Failure", The Journal of the Japan Medical Association, vol. 130, No. 1, 2003, pp. 40-45.

* cited by examiner

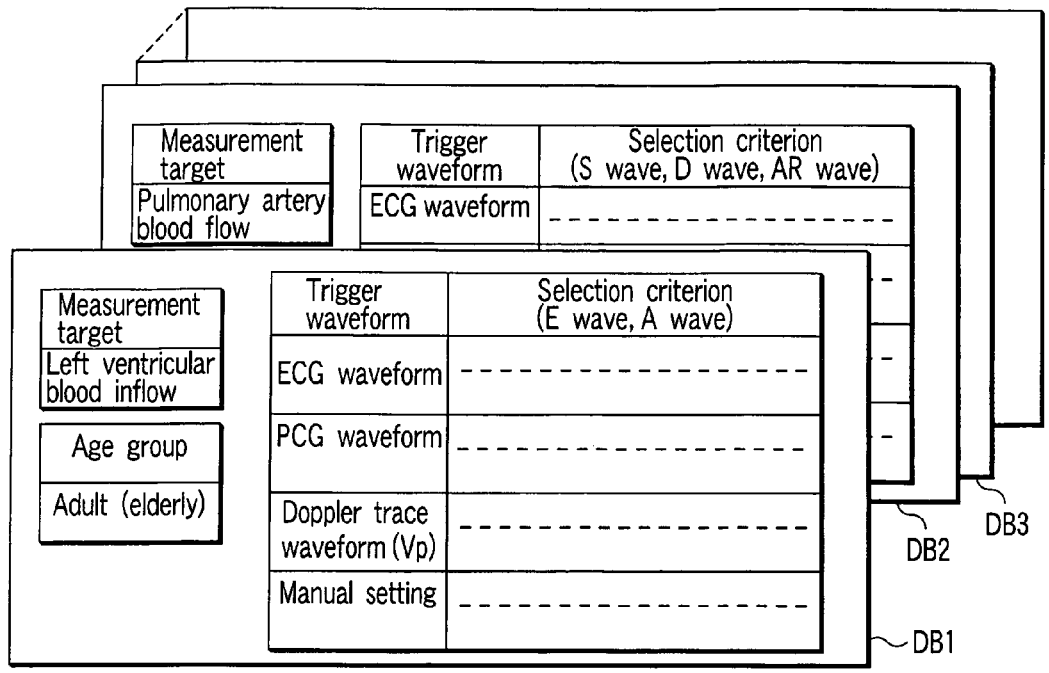

FIG. 7

| Trigger waveform | Selection criterion (E wave, A wave) |
|---|---|
| ECG waveform | Local maximum/minimum pairs of trace waveform are searched out with reference to 40% of cardiac cycle T0 from R wave of ECG signal as reference position, and two coordinates having maximum and second maximum are detected, thereby selecting maximum coordinate following reference position as E wave, and maximum coordinate following E wave as A wave |
| PCG waveform | Maximum/minimum pairs of trace waveform are searched out with reference to S1 or S2 of PCG waveform as reference position, and two coordinates having maximum and second local maximum are detected, thereby selecting maximum coordinate following reference position as E wave, and local maximum coordinate following E wave as A wave |
| Trace waveform (Vp) | Two coordinates exhibiting maximum and second local maximum in trace waveform are detected, and when distance between two coordinates is shorter than cardiac cycle T0, temporally preceding local maximum coordinate in the same cardiac cycle is selected as E wave, and local maximum coordinate following E wave is selected as A wave |
| Manual setting | Local maximum/minimum pairs of trace waveform are searched out with reference to manually designated position as reference position, and two coordinates having maximum and second local maximum are detected, thereby selecting local maximum coordinate following reference position as E wave, and local maximum coordinate following E wave as A wave |

FIG. 8

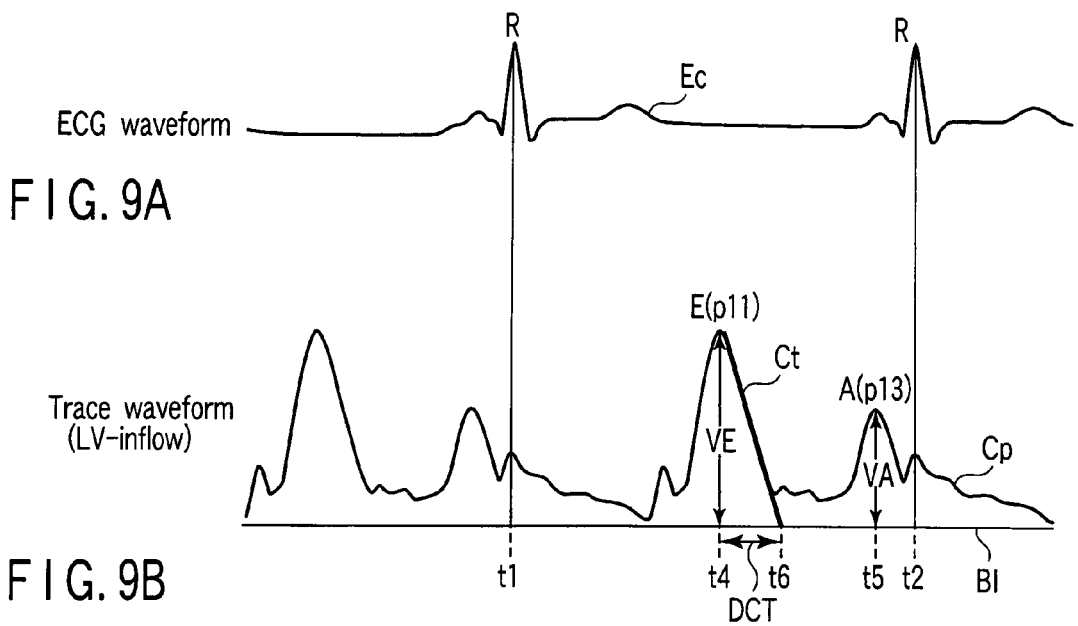
F I G. 9A
F I G. 9B
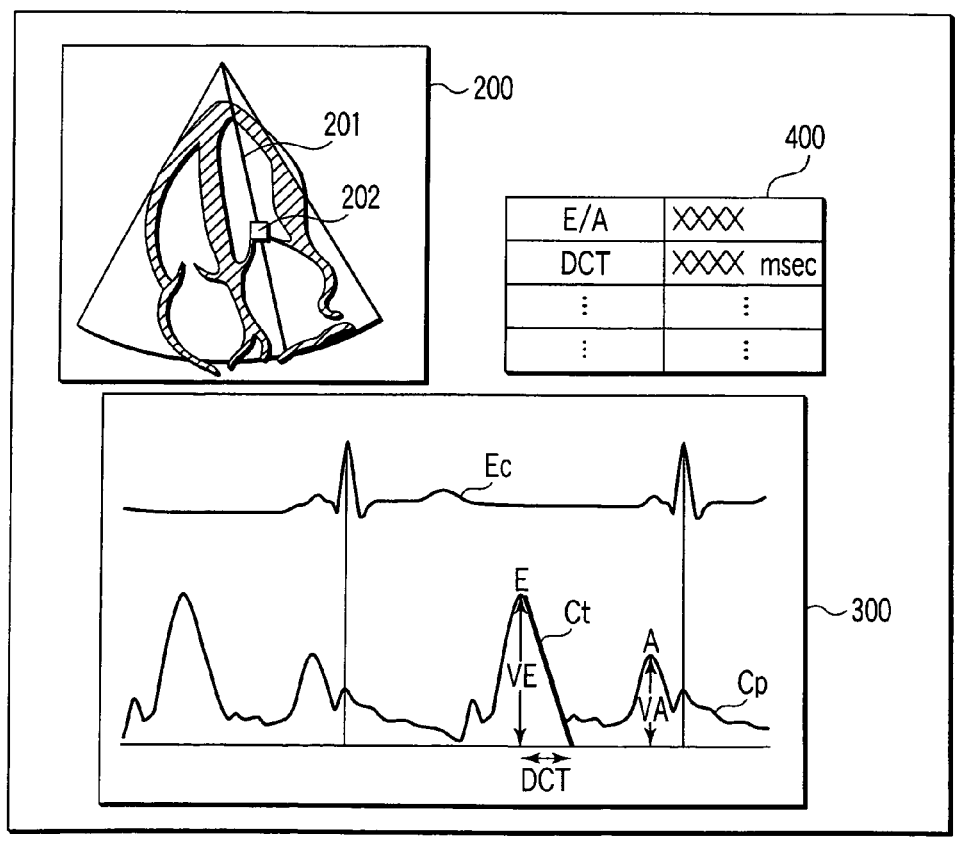
F I G. 10

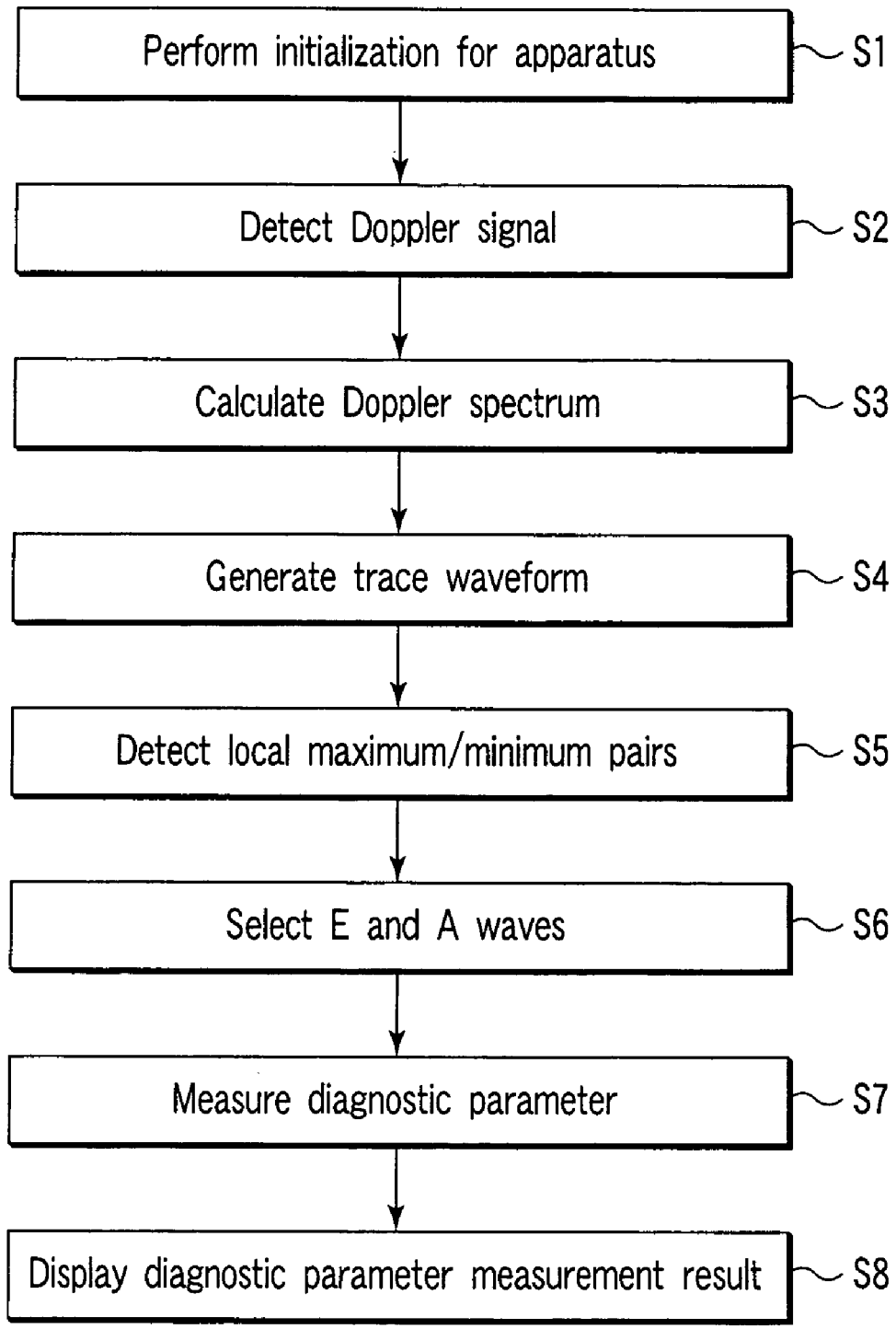
F I G. 11

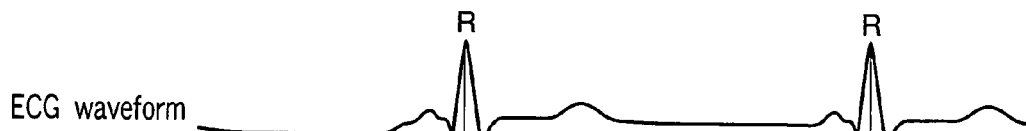

FIG. 12A

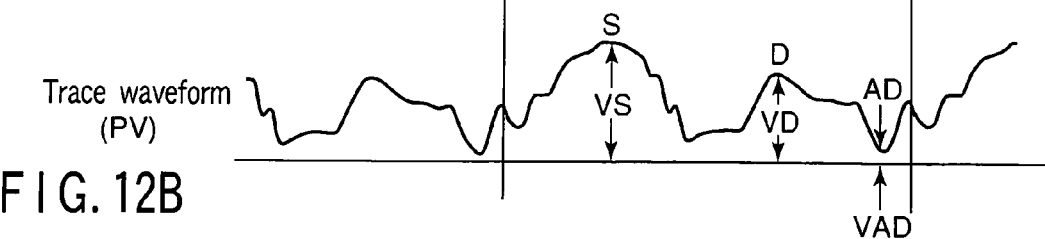

FIG. 12B

| Trigger waveform | Selection criterion (S wave, D wave, AR wave) |
|---|---|
| ECG waveform | Local maximum/minimum pairs of trace waveform are searched out with reference to 40% of cardiac cycle T0 from R wave of ECG signal as reference position, and two coordinates having maximum and second local maximum are detected, thereby selecting local maximum coordinate following reference position as S wave, local maximum coordinate following S wave as A wave, and local minimum coordinate forming local maximum/minimum pair, together with S wave, as AR wave |
| PCG waveform | Local Maximum/minimum pairs of trace waveform are searched out with reference to S1 of PCG waveform as reference position, and two coordinates having maximum and second local maximum are detected, thereby selecting local maximum coordinate following reference position as S wave, and local maximum coordinate following S wave as D wave, or local maximum/minimum pairs of trace waveform are searched out with reference to S2 of PCG waveform as reference position, and two coordinates having maximum and second local maximum are detected, thereby selecting local maximum coordinate following reference position as D wave, and local maximum coordinate following D wave as S wave |
| Trace waveform (Vp) | Two coordinates exhibiting maximum and second local maximum in trace waveform are detected, and when distance between two coordinates is shorter than cardiac cycle T0, temporally preceding local maximum coordinate in the same cardiac cycle is selected as S wave, and local maximum coordinate following S wave is selected as D wave |
| Manual setting | Local Maximum/minimum pairs of trace waveform are searched out with reference to manually designated position as reference position, and two coordinates having maximum and second local maximum are detected, thereby selecting local maximum coordinate following reference position as S wave, and local maximum coordinate following S wave as D wave |

FIG. 13

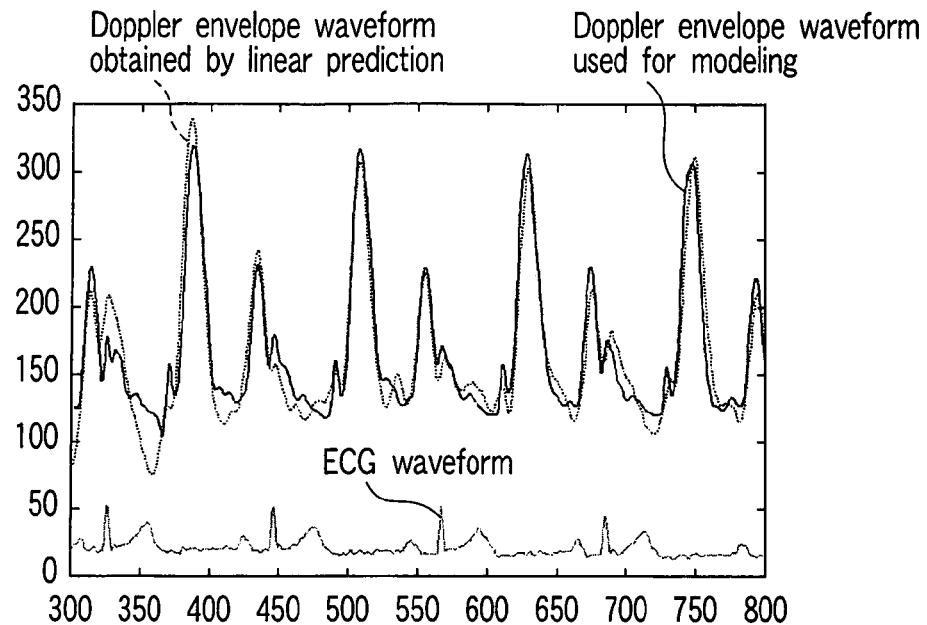
F I G. 20
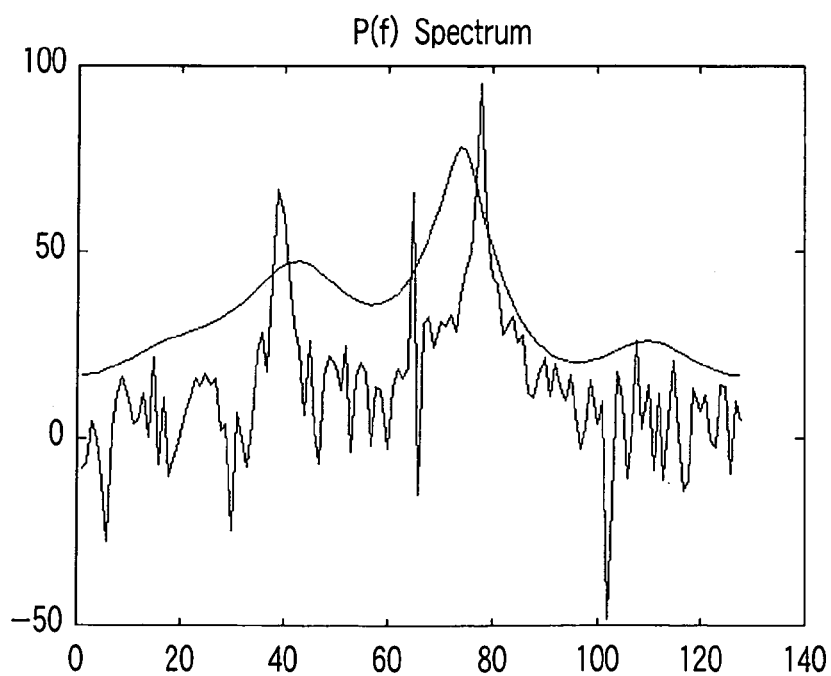
F I G. 21

Time-series residual square sum

MT method, MTA method, MTS method

Example of diagnostic DB of ages, diagnosis regions, and measurement parameters (normal case)

Table left ventricular filling dynamics in normal case

|  | <Age 50 (n=61) | ≧Age 50 (n=56) | P value |
|---|---|---|---|
| Left ventricular inflow | | | |
|   Maximum E (cm/s) | 72±14 | 62±14 | <0.01 |
|   Maximum A (cm/s) | 40±10 | 69±141 | <0.01 |
|   E/A | 1.9±0.6 | 1.1±0.3 | <0.01 |
|   DT (ms) | 179±20 | 210±36 | <0.01 |
|   IVRT (cm/s) | 76±11 | 90±17 | <0.01 |
| Pulmonary artery | (n=44) | (n=41) | |
|   Maximum S (cm/s) | 48±9 | 71±9 | <0.01 |
|   Maximum D (cm/s) | 50±10 | 38±9 | <0.01 |
|   Maximum AR (cm/s) | 19±4 | 23±14 | <0.01 |

(Quoted from Klein A.L. and Cohen.G.I.: Doppler echocardiographic assessment of constrictive pericarditis, cardiac amyloielesis, and cardiac tarrponade Cleve.Clin.J.Med.59 : 281, 1992)

FIG. 27

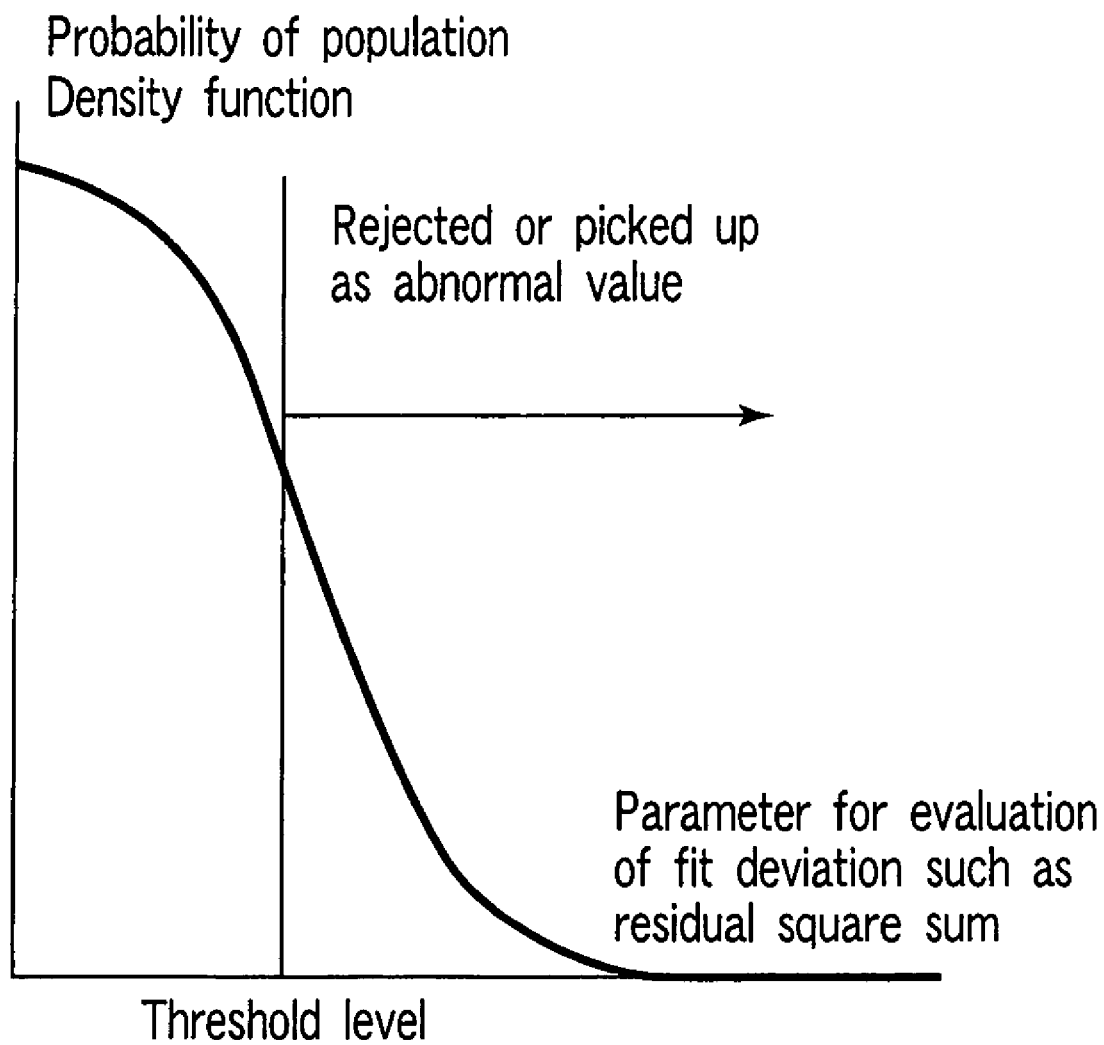
F I G. 30

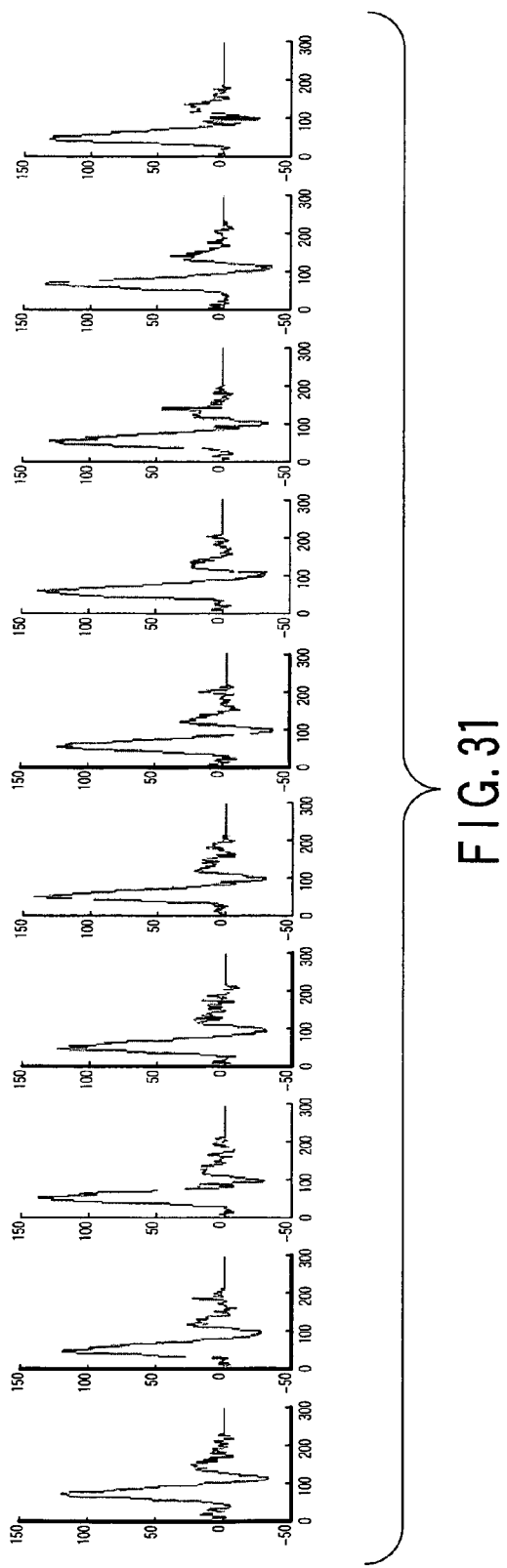
F I G. 31

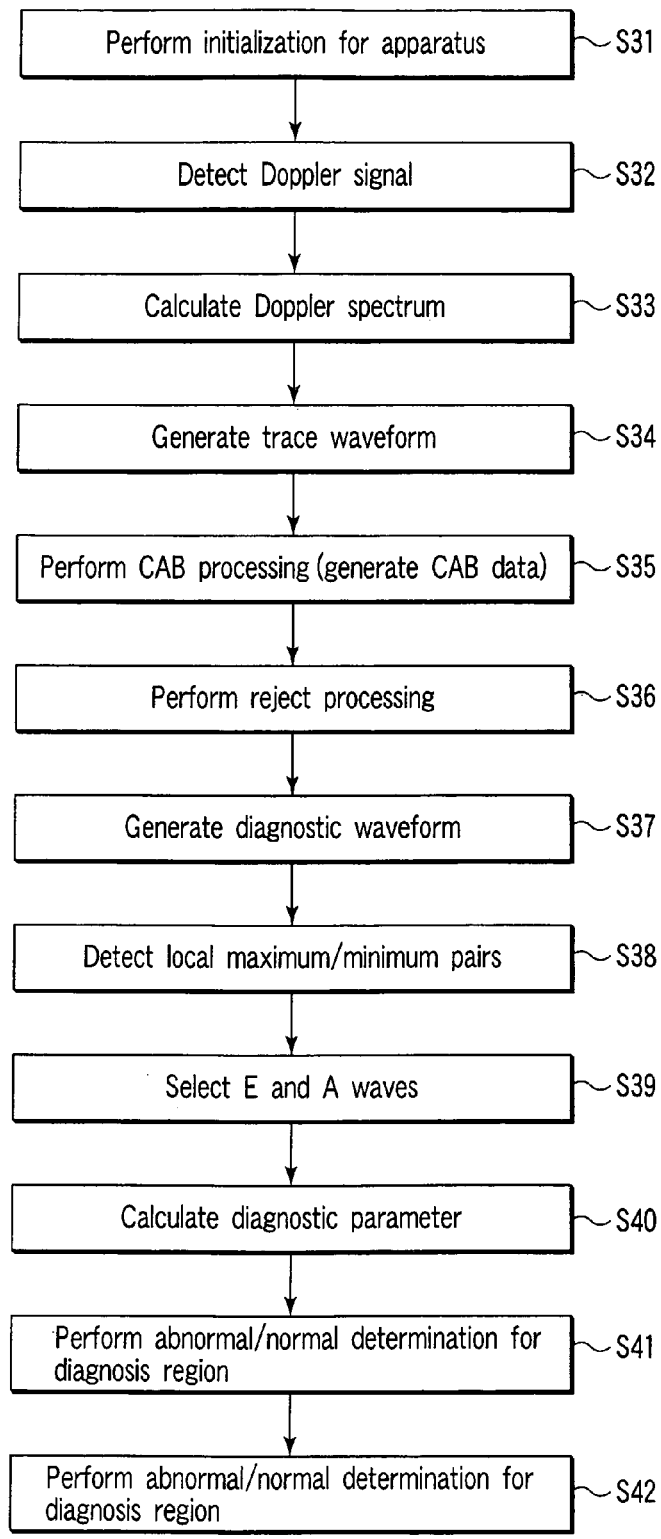
F I G. 35

ULTRASONIC DOPPLER DIAGNOSTIC APPARATUS AND MEASURING METHOD OF DIAGNOSTIC PARAMETER

BACKGROUND OF THE INVENTION

The present invention relates to an ultrasonic Doppler diagnostic apparatus which measures the flow velocity information of a blood flow and the movement information of tissue in a living body by using the Doppler effect of ultrasonic waves, and a measuring method of diagnostic parameter.

An ultrasonic diagnostic apparatus is designed to apply ultrasonic pulses generated by piezoelectric transducers incorporated in an ultrasonic probe into an object to be examined, receive reflected ultrasonic waves generated by the difference in acoustic impedance between object tissues through the piezoelectric transducers, and display the resultant image on a monitor. This diagnostic method allows easy observation of a real-time two-dimensional image by simple operation of only bringing the ultrasonic probe into contact with the body surface, and hence is widely used for functional diagnosis or morphological diagnosis of various organs of a living body. Ultrasonic diagnostic methods of obtaining living body information by using reflected waves from tissue or blood cells in a living body have rapidly progressed along with two great technical developments of an ultrasonic pulse reflection method and ultrasonic Doppler method. B mode images and color Doppler images obtained by these techniques have become indispensable to recent ultrasonic image diagnosis.

A Doppler spectrum method is available as a method of obtaining blood flow information at an arbitrary position in an object quantitatively with high accuracy. In this Doppler spectrum method, ultrasonic wave transmission/reception is performed with respect to the same region of an object at predetermined intervals a plurality of number of times, and Doppler signals are detected by performing quadrature phase detection for reflected ultrasonic waves from moving reflectors such as blood cells by using a reference signal having a frequency almost equal to the resonance frequency of the piezoelectric transducers used for ultrasonic wave transmission/reception. A Doppler signal in the desired region is extracted from these Doppler signals by using a range gate. A Doppler spectrum is calculated by FFT-analyzing the extracted Doppler signal.

Doppler spectra are continuously calculated with respect to Doppler signals obtained from a desired region of an object by this sequence, and the plurality of obtained Doppler spectra are sequentially arrayed to generate Doppler spectrum data. In general, in order to accurately set a range gate at a desired observation region of an object, the range gate is set under B mode image observation. At this time, the range gate position is displayed on the B mode image.

The Doppler spectrum data obtained by this ultrasonic Doppler diagnostic apparatus is generally displayed with the ordinate representing a frequency (f), the abscissa representing time (t), and the power (intensity) of each frequency component being represented by a luminance (gray level). Various kinds of diagnostic parameters are measured on the basis of this Doppler spectrum data. For example, a maximum blood flow velocity Vp corresponding to a maximum frequency component fp in the frequency axis direction or the position of an average flow velocity Vc corresponding to an average frequency component fc is detected with respect to each of temporally continuously obtained Doppler spectra, and a trace waveform representing a temporal change in the maximum blood flow velocity Vp or average flow velocity Vc is generated.

When a blood flow in a blood vessel such as a carotid is to be evaluated, a waveform peak PS (Peak of Systolic) which occurs in a trace waveform in a systole and a waveform peak ED (End of Diastolic) which occurs in a diastole are detected. HR (Heart Rate) of an intravascular blood flow is measured on the basis of the position information of PS or ED. In addition, PI (Pulsatility Index), RI (Resistance Index), and the like as diagnostic parameters for a peripheral vessel are measured from a trace waveform in a cardiac cycle set by PS or ED.

Note that the generation of the trace waveform of Vp or Vc, the detection of PS/ED, and the measurement of a diagnostic parameter such as PI or RI, described above, are basically performed by manual operation with respect to frozen (freeze-displayed) Doppler spectrum data in the prior art. Recently, however, as disclosed in, for example, Jpn. Pat. Appln. KOKAI Publication No. 2003-284718, it has become possible that Vp or Vc be automatically traced or HR, PI, or RI be automatically measured with respect to Doppler spectrum data display in real time.

BRIEF SUMMARY OF THE INVENTION

For cardiac function evaluation as well, in daily examination, Doppler spectrum data is generated with respect to a left ventricular blood inflow (LV-Inflow), pulmonary artery blood flow (PV), or the like, and various kinds of diagnostic parameters are measured on the basis of the trace waveforms of the maximum blood flow velocity Vp and average flow velocity Vc in the Doppler spectrum data.

As diagnostic parameters in the above left ventricular blood inflow measurement, an amplitude ratio "E/A" between E and A waves of the trace waveform of the maximum blood flow velocity Vp, and a descending period "DCT" of an E wave are used. As diagnostic parameters in the pulmonary artery blood flow measurement, a velocity "VS" of an S wave, a velocity "VD" of a D wave, and a velocity "VAR" of an AR wave are used.

The above diagnostic parameter measurement is conventionally performed with respect to a trace waveform in a desired period which is read out from a cine memory in which the trace waveform obtained by the ultrasonic diagnostic apparatus is temporarily stored.

Conventionally, for example, after a trace waveform in a desired period is selected by sequentially reading out trace waveforms stored in a cine memory, two time cursors are placed on the trace waveform in the desired period which is statically displayed on a display unit, thereby setting one cardiac cycle (e.g., an ED-ED interval), selecting E and A waves in the trace waveform in this one cardiac cycle, and setting a tangent for "DCT" measurement.

However, the above processing in conventional diagnostic parameter measurement is performed by manual operation by an operator, and hence cumbersome operation is required. In particular, it is difficult to automate the selection of E and A waves in left ventricular blood inflow measurement and S, D, and AR waves in pulmonary artery blood flow measurement, as compared with the selection of PS and ED which has already been described, because pattern recognition is required.

That is, manual operation in the conventional measuring method of diagnostic parameter requires a long period of time and decreases the efficiency of cardiac function measurement. This also makes it impossible to measure Doppler spectrum data displayed in real time. In addition; the diagnostic parameter measurement accuracy based on this manual operation depends on the experience of an operator, and hence sufficient reproducibility cannot be obtained.

The present invention has been made in consideration of such conventional problems, and has as its object to provide an ultrasonic Doppler diagnostic apparatus in which when cardiac function measurement is to be performed on the basis of the trace waveform of a Doppler spectrum, an improvement in measurement accuracy and a reduction in measurement time can be achieved by automatically measuring diagnostic parameters effective for the measurement, and a measuring method of diagnostic parameter.

According to an aspect of the present invention, there is provided an ultrasonic Doppler diagnostic apparatus comprising a Doppler signal detecting unit which detects a Doppler signal at a predetermined region from a reception signal obtained by performing ultrasonic wave transmission/reception with respect to an object to be examined, a spectrum calculating unit which calculates a frequency spectrum of the Doppler signal, a trace waveform generating unit which generates a trace waveform representing a temporal change in a predetermined spectrum component in the frequency spectrum, a CAB processing unit which generates CAB data by extracting a trace waveform for each cardiac cycle from the generated trace waveform, and arraying the plurality of extracted trace waveforms along a first time axis representing a time direction associated with a heart rate and a second time axis representing a time direction within one cardiac cycle, a statistical processing unit which generates a diagnostic waveform by performing statistical processing using the CAB data, a storage unit which stores a selection criterion, a feature amount selecting unit which automatically selects a feature amount for the diagnostic waveform on the basis of the stored selection criterion, a diagnostic parameter measuring unit which measures a diagnostic parameter on the basis of the feature amount, and a display unit which displays a measurement result on the diagnostic parameter.

According to another aspect of the present invention, there is provided an ultrasonic Doppler diagnostic apparatus comprising a Doppler signal detecting unit which detects a Doppler signal at a predetermined region from a reception signal obtained by performing ultrasonic wave transmission/reception with respect to an object to be examined, a spectrum calculating unit which calculates a frequency spectrum of the Doppler signal, a trace waveform generating unit which generates a trace waveform representing a temporal change in a predetermined spectrum component in the frequency spectrum, a storage unit which stores a selection criterion, a feature amount selecting unit which automatically selects a feature amount with respect to the trace waveform in a predetermined cardiac cycle of the object on the basis of the stored selection criterion, a diagnostic parameter measuring unit which measures a diagnostic parameter on the basis of the feature amount, and a display unit which displays a measurement result on the diagnostic parameter.

According to another aspect of the present invention, there is provided a measuring method of diagnostic parameter comprising detecting a Doppler signal at a predetermined region from a reception signal obtained by performing ultrasonic wave transmission/reception with respect to an object to be examined, calculating a frequency spectrum of the Doppler signal, generating a trace waveform representing a temporal change in a predetermined spectrum component in the frequency spectrum, generating CAB data by extracting a trace waveform for each cardiac cycle from the generated trace waveform, and arraying the plurality of extracted trace waveforms along a first time axis representing a time direction associated with a heart rate and a second time axis representing a time direction within one cardiac cycle, generating a diagnostic waveform by performing statistical processing using the CAB data, automatically selecting a feature amount with respect to the diagnostic waveform on the basis of a stored selection criterion, measuring a diagnostic parameter on the basis of the feature amount, and displaying a measurement result on the diagnostic parameter.

According to another aspect of the present invention, there is provided a measuring method of diagnostic parameter comprising detecting a Doppler signal at a predetermined region from a reception signal obtained by performing ultrasonic wave transmission/reception with respect to an object to be examined, calculating a frequency spectrum of the Doppler signal, generating a trace waveform representing a temporal change in a predetermined spectrum component in the frequency spectrum, automatically selecting a feature amount with respect to the trace waveform in a predetermined cardiac cycle of the object on the basis of a stored selection criterion, measuring a diagnostic parameter on the basis of the feature amount, and displaying a measurement result on the diagnostic parameter.

BRIEF DESCRIPTION OF THE SEVERAL VIEWS OF THE DRAWING

FIG. 7 is a view schematically showing a database of selection criteria in a feature amount selecting unit in the first embodiment;

FIG. 8 is a view showing a specific example of selection criteria in left ventricular blood inflow measurement in the first embodiment;

FIGS. 9A and 9B are graphs showing a method of measuring diagnostic parameters which is performed for a trace waveform in left ventricular blood inflow measurement in the first embodiment;

FIG. 10 is a view showing a specific example of a display method in a display unit in the first embodiment;

FIG. 11 is a flowchart showing a sequence for measuring diagnostic parameters in the first embodiment;

FIGS. 12A and 12B are graphs showing a trace waveform in pulmonary artery blood flow measurement in a modification of the first embodiment;

FIG. 13 is a view showing selection criteria in pulmonary artery blood flow measurement in a modification to the first embodiment;

FIG. 20 is a graph showing an example of a diagnostic waveform obtained by ARX time axis model calculation processing;

FIG. 21 is a graph for explaining a frequency parametric model;

FIG. 27 is a view showing an example of normal values of various kinds of measurement parameters stored in a diagnostic database;

FIG. 30 is a graph for explaining a reject function which the ultrasonic Doppler diagnostic apparatus according to the third embodiment has;

FIG. 31 is a graph for explaining a manual reject function;

FIG. 35 is a flowchart showing the flow of processing executed by this ultrasonic Doppler diagnostic apparatus using the reject function.

DETAILED DESCRIPTION OF THE INVENTION

Figure 1:
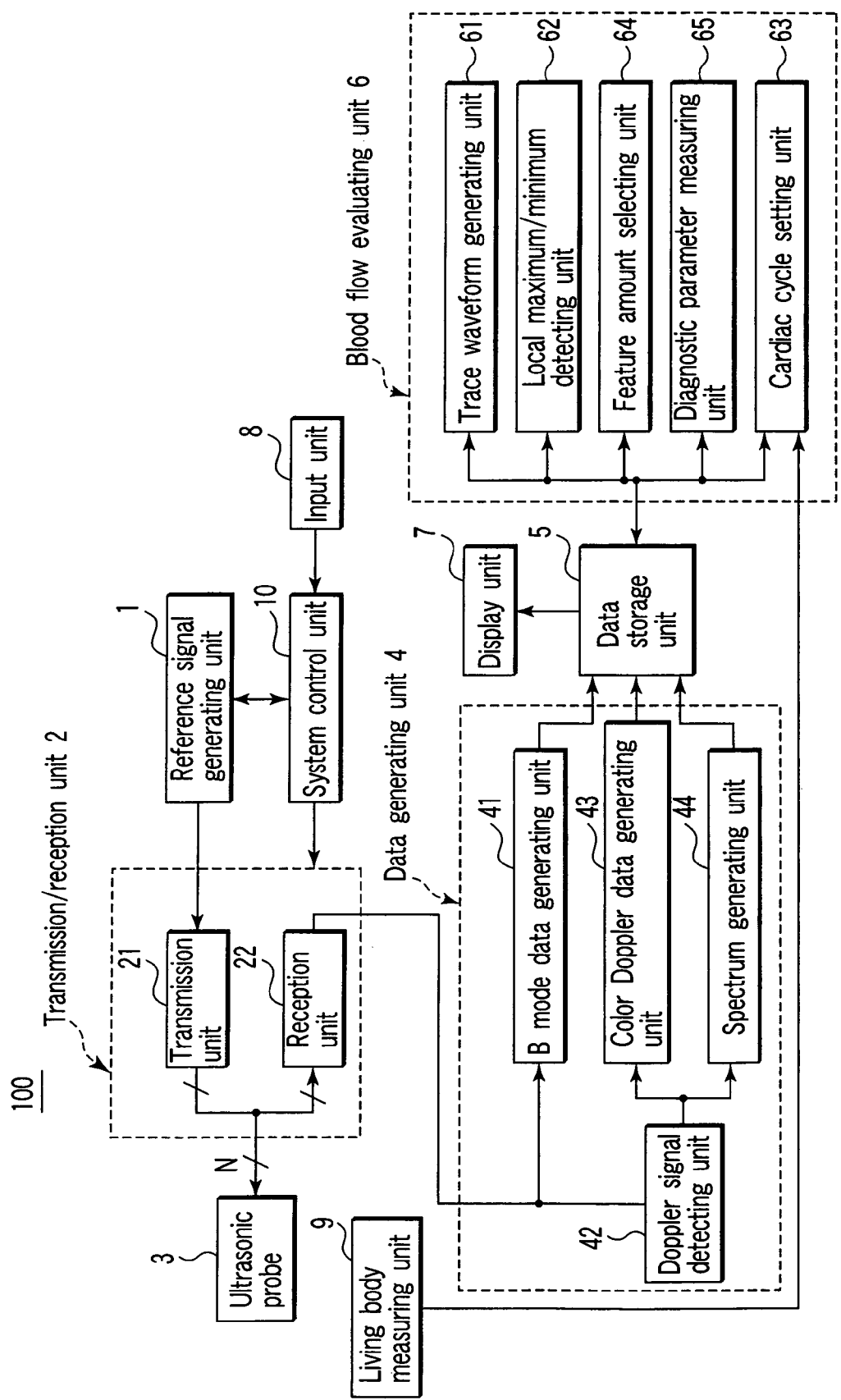
FIG. 1 is a block diagram showing the overall arrangement of an ultrasonic Doppler diagnostic apparatus according to the first embodiment.

The first to third embodiments of the present invention will be described below with reference to the views of the accompanying drawing. Note that the same reference numerals in the following description denote constituent elements having substantially the same functions and arrangements, and a repetitive description will be made only when required.

(First Embodiment)

The first embodiment of the present invention will be described below with reference to the views of the accompanying drawing.

(Arrangement of Apparatus)

In the following embodiment of the present invention, a plurality of local maximum/minimum pairs are detected with respect to the trace waveform of a maximum blood flow velocity Vp generated with respect to the Doppler spectrum data of a left ventricular blood inflow, and an E wave and A wave as feature amounts are selected, on the basis of a selection criterion stored in advance as database data, from a plurality of local maximum/minimum pairs in a predetermined cardiac cycle set on the basis of an ECG signal. Diagnostic parameters "E/A" and "DCT" are measured by using the position information or velocity information of the selected E and A waves.

Figure 2:
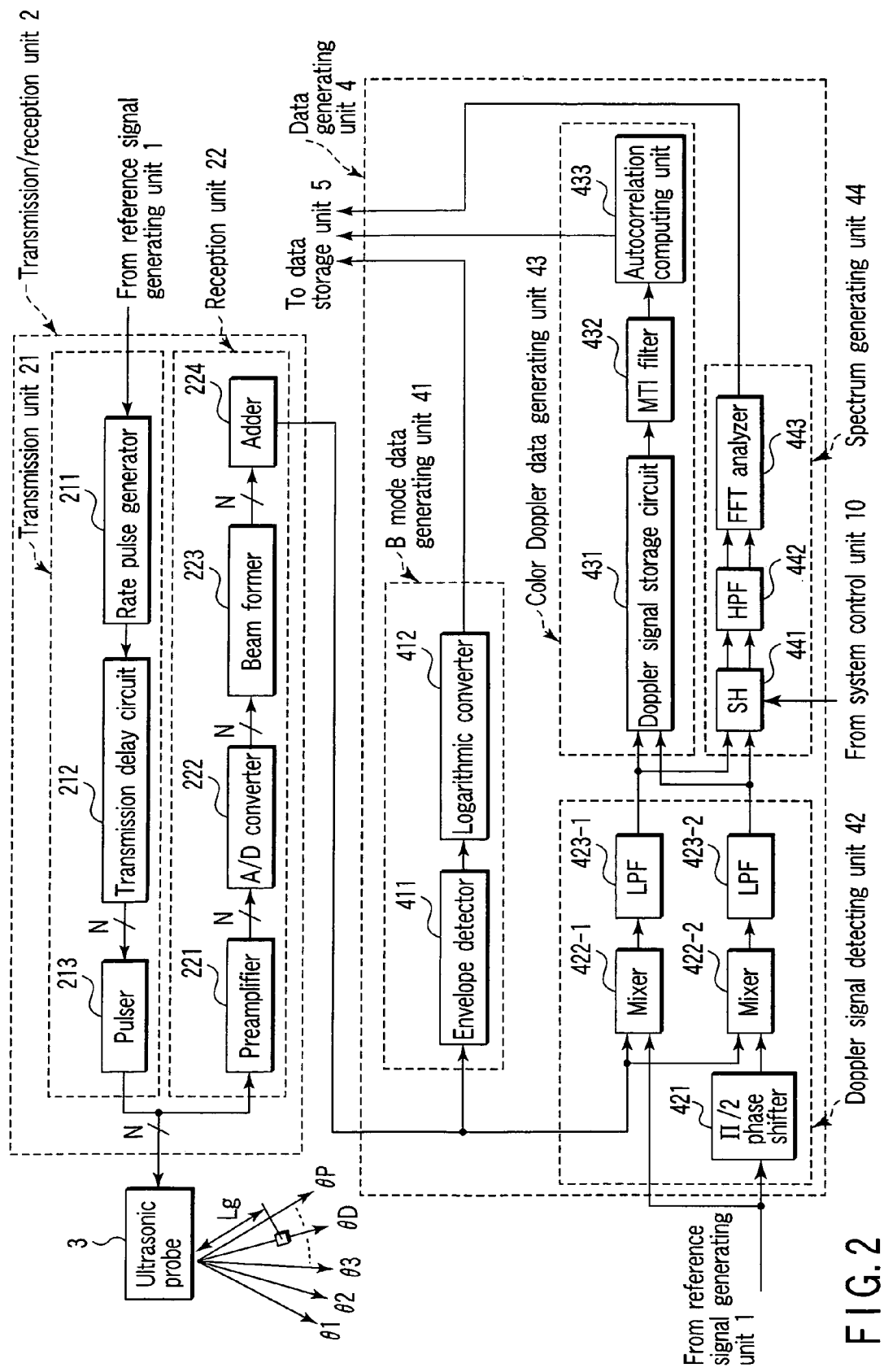
FIG. 2 is a block diagram showing the arrangements of a transmission/reception unit and data generating unit in the first embodiment.

The arrangement of an ultrasonic Doppler diagnostic apparatus and the basic operation of each unit in an embodiment of the present invention will be described below with reference to FIGS. 1 to 10. FIG. 1 is a block diagram showing the overall arrangement of the ultrasonic Doppler diagnostic apparatus according to this embodiment. FIG. 2 is a block diagram of a transmission/reception unit and data generating unit which constitute this ultrasonic Doppler diagnostic apparatus.

An ultrasonic Doppler diagnostic apparatus 100 shown in FIG. 1 comprises an ultrasonic probe 3 which transmits/receives ultrasonic waves to/from an object to be examined, a transmission/reception unit 2 which performs transmission/reception with respect to the ultrasonic probe 3, and a data generating unit 4 which performs signal processing for obtaining B mode data, color Doppler image data, and a Doppler spectrum from reception signals obtained from the transmission/reception unit 2. This apparatus further comprises a blood flow evaluating unit 6 which generates the trace waveform of a maximum blood flow velocity Vp or average flow velocity Vc on the basis of the Doppler spectrum obtained by a data generating unit 4, and measures various kinds of diagnostic parameters in cardiac function measurement on the basis of the trace waveform, and a data storage unit 5 which stores the various kinds of data generated by the data generating unit 4, the trace waveform generated by the blood flow evaluating unit 6 or measurement results of various kinds of diagnostic parameters in the blood flow evaluating unit 6, and the like.

The ultrasonic Doppler diagnostic apparatus 100 also comprises a reference signal generating unit 1 which generates, for example, a continuous or rectangular wave having a frequency almost equal to the center frequency of ultrasonic pulses with respect to the transmission/reception unit 2 or data generating unit 4, a display unit 7 which displays, for example, the image data or Doppler spectrum generated by the data generating unit 4 and the trace waveform generated by the blood flow evaluating unit 6 or measurement results of diagnostic parameters in the blood flow evaluating unit 6, and the like, an input unit 8 which is used by an operator to, for example, input patient information, select an image display mode, measurement mode, and trigger waveform, set ultrasonic data acquisition conditions, and input various kinds of command signals, a living body measuring unit 9 which acquires the heartbeat information of an object to be examined, and a system control unit 10 which systematically controls the above respective units of the ultrasonic Doppler diagnostic apparatus 100.

The ultrasonic probe 3 transmits/receives ultrasonic waves to/from the surface of the object while the front surface of the probe is in contact with the surface of the object, and has a one-dimensional array of a plurality of (N) minute piezoelectric transducers at the distal end portion of the probe. Each piezoelectric transducer is an electroacoustic conversion element, which has a function of converting an electrical pulse into an ultrasonic pulse (transmission ultrasonic wave) at the time of transmission and converting a reflected ultrasonic wave (reception ultrasonic wave) into an electrical signal (reception signal) at the time of reception. The ultrasonic probe 3 is designed to be small in size and weight and is connected to a transmission unit 21 and reception unit 22 of the transmission/reception unit 2 through cables. The ultrasonic probe 3 includes probes for sector scanning, linear scanning, and convex scanning, one of which is arbitrarily selected in accordance with a diagnosis region. The following description will exemplify the ultrasonic probe 3 for sector scanning directed to cardiac function measurement. However, the present invention is not limited to this, and this probe may be that for linear scanning or convex scanning.

The transmission/reception unit 2 shown in FIG. 2 comprises the transmission unit 21 which generates a driving signal for making the ultrasonic probe 3 emit transmission ultrasonic waves and the reception unit 22 which performs phased addition of reception signals from the ultrasonic probe 3.

The transmission unit 21 comprises a rate pulse generator 211, transmission delay circuit 212, and pulser 213. The rate pulse generator 211 generates a rate pulse for determining the repetition period of transmission ultrasonic waves by frequency-dividing a continuous wave or rectangular wave supplied from the reference signal generating unit 1, and supplies the rate pulse to the transmission delay circuit 212.

The transmission delay circuit 212 is comprised of independent delay circuits equal in number to the piezoelectric transducers (N channels) used for transmission. The transmission delay circuit 212 gives a rate pulse a delay time for focusing a transmission ultrasonic wave to a predetermined depth so as to obtain a small beam width at the time of transmission and a delay time for applying a transmission ultrasonic wave in a predetermined direction, and supplies the resultant rate pulse to the pulser 213. The pulser 213 has independent driving circuits corresponding to N channels, and generates driving pulses for driving the piezoelectric transducers incorporated in the ultrasonic probe 3 on the basis of the rate pulse.

The reception unit 22 comprises a preamplifier 221, A/D converter 222, beam former 223, and adder 224 each comprising N channels. The preamplifier 221 ensures a sufficient S/N by amplifying a small signal converted into an electrical reception signal by each ultrasonic transducer. The N-channel reception signals amplified to a predetermined magnitude by the preamplifier 221 are converted into digital signals by the A/D converter 222. The resultant signals are sent to the beam former 223.

The beam former 223 gives each of the N-channel reception signals output from the A/D converter 222 a focusing delay time for focusing a reflected ultrasonic wave from a predetermined depth and a deflection delay time for setting reception directivity with respect to a predetermined direction. The adder 224 then performs phased addition of reception signals from the beam former 223 (addition of reception signals obtained from a predetermined direction upon phase matching).

The data generating unit 4 comprises a B mode data generating unit 41 which generates B mode data with respect to the reception signal output from the adder 224 of the reception unit 22, a Doppler signal detecting unit 42 which detects a Doppler signal by performing quadrature detection of the reception signal, a color Doppler data generating unit 43 which generates color Doppler data on the basis of the detected Doppler signal, and a spectrum data calculating unit 44 which calculate the frequency spectrum of the Doppler signal.

The B mode data generating unit 41 comprises an envelope detector 411 and logarithmic converter 412. The envelope detector 411 performs envelope detection of the reception signal after phased addition which is supplied from the adder 224 of the reception unit 22. The amplitude of this envelope detection signal is logarithmically converted by the logarithmic converter 412. In general, a reception signal from the inside of the object has an amplitude with a wide dynamic range of 80 dB or more. When such a signal is to be displayed on a TV monitor having a dynamic range of about 30 dB, the amplitude of the signal needs to be compressed by logarithmic conversion.

The Doppler signal detecting unit 42 comprises a $\pi/2$ phase shifter 421, mixers 422-1 and 422-2, and LPFs (Low-Pass Filters) 423-1 and 423-2, and detects a Doppler signal by performing quadrature phase detection for the reception signal supplied from the adder 224 of the reception unit 22 by the operation to be described later.

The color Doppler data generating unit 43 comprises a Doppler signal storage circuit 431, MTI filter 432, and autocorrelation computing unit 433. A Doppler signal from the Doppler signal detecting unit 42 is temporarily stored in the Doppler signal storage circuit 431. The MTI filter 432 as a high-pass digital filter reads out a Doppler signal stored in the Doppler signal storage circuit 431, and removes a Doppler component (a clutter component) due to the respiratory movement or pulsatory movement of an organ or the like from the Doppler signal. The autocorrelation computing unit 433 calculates the autocorrelation value of the Doppler signal obtained by extracting only blood flow information using the MTI filter 432, and further calculates the average flow velocity value or variance of a blood flow on the basis of the autocorrelation value.

The spectrum data calculating unit 44 comprises an SH (Sample/Hold circuit) 441, HPF (High-Pass Filter) 442, and FFT (Fast-Fourier-Transform) analyzer 443, and performs FFT analysis for the Doppler signal obtained by the Doppler signal detecting unit 42. Note that the SH 441 and HPF 442 each are comprised of two channels, to each of which the complex components of the Doppler signal output from the Doppler signal detecting unit 42, i.e., a real component (I component) and imaginary component (Q component), are supplied.

Figure 3:
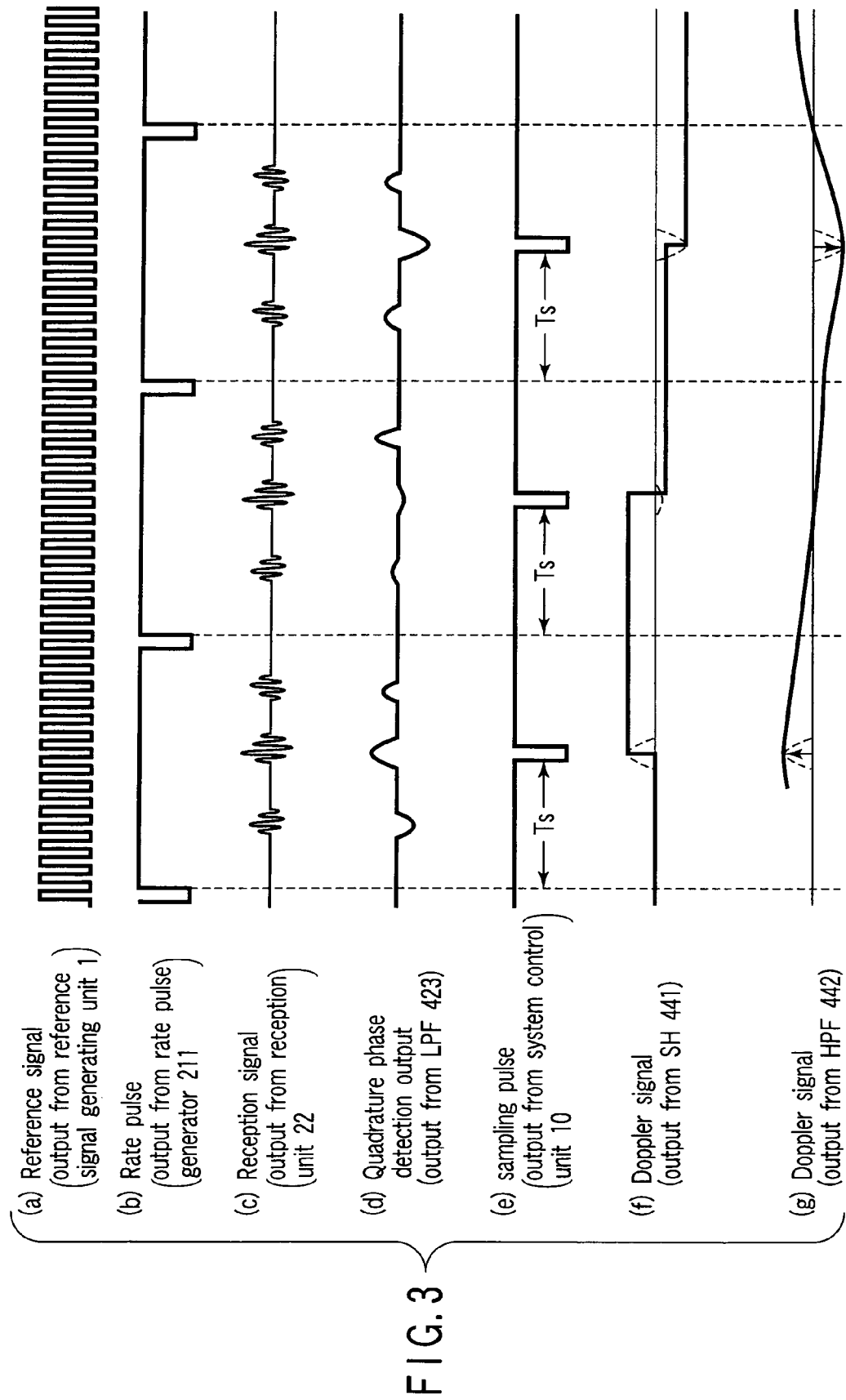
FIG. 3 is a timing chart showing the basic operations of a Doppler signal detecting unit and spectrum calculating unit in the first embodiment.

The basic operations of the Doppler signal detecting unit 42 and spectrum data calculating unit 44 which are important constituent elements for the generation of a Doppler spectrum in the present invention will be described in detail next with reference to the timing chart of FIG. 3. For the sake of easy explanation, FIG. 3 shows a case wherein a Doppler component is detected from an analog reception signal. In actual processing, however, such detection is performed with respect to a digital reception signal output from the reception unit 22.

Referring to FIG. 3, reference symbol (a) denotes a reference signal output from the reference signal generating unit 1; (b), a rate pulse for a Doppler spectrum which is output from the rate pulse generator 211 of the transmission/reception unit 2; and (c), a reception signal after phased addition which is obtained from the adder 224 of the reception unit 22.

In addition, reference symbol (d) denotes a quadrature phase detection output from the LPF 423 of the Doppler signal detecting unit 42; (e), a sampling pulse which is supplied from the system control unit 10 to set a sampling (range gate) position of the SH 441 in the spectrum data calculating unit 44; (f), a Doppler signal sampled/held by the SH 441; and (g), a Doppler signal in a range gate smoothed by the HPF 442.

The reception signal ((c) in FIG. 3) output from the reception unit 22 in FIG. 2 is input to the first input terminal of each of the mixers 422-1 and 422-2 of the Doppler signal detecting unit 42. On the other hand, the reference signal ((a) in FIG. 3) which is generated by the reference signal generating unit 1 and has a repetition frequency almost equal to the center frequency of this reception signal is directly supplied to the second input terminal of the mixer 422-1, and the reference signal obtained by 90° phase shift in the n/2 phase shifter 421 is sent to the second input of the mixer 422-2. The outputs from the mixers 422-1 and 422-2 are sent to the LPFs 423-1 and 423-2, and the sum component of the frequency of the reception signal supplied from the reception unit 22 and the repetition frequency of the reference signal supplied from the reference signal generating unit 1 is removed, and only the difference component is extracted as a Doppler signal ((d) in FIG. 3).

The Doppler signals output from the LPFs 423-1 and 423-2 and the sampling pulse (range gate pulse) generated by the system control unit 10 by frequency-dividing the reference signal from the reference signal generating unit 1 are supplied to the SH 441 ((e) in FIG. 3). A Doppler signal from a desired distance is sampled/held with this sampling pulse ((f) in FIG. 3). Note that this sampling pulse is generated a delay time Ts after the rate pulse ((b) in FIG. 3) for determining the timing of the emission of a transmission ultrasonic wave. The delay time Ts can be arbitrarily set by the input unit 8.

By changing the delay time Ts of the sampling pulse, the operator can extract a Doppler signal at a desired distance Lg from the ultrasonic probe 3. Note that letting C be the sound velocity of an object, the delay time Ts and desired distance Lg have the relationship represented by 2Lg/C=Ts.

The staircase noise component superimposed on the Doppler signal at the desired distance Lg output from the SH 441 is removed by the HPF 442 ((g) in FIG. 3), and the smoothed Doppler signal is supplied to the FFT analyzer 443 to generate a frequency spectrum (a Doppler spectrum).

The FFT analyzer 443 comprises a computing circuit and storage circuit (not shown), and temporarily stores, in the storage circuit, the Doppler signal output from the HPF 442. The computing circuit performs FFT analysis in a predetermined period of a series of Doppler signals stored in this storage circuit.

Figure 4A:
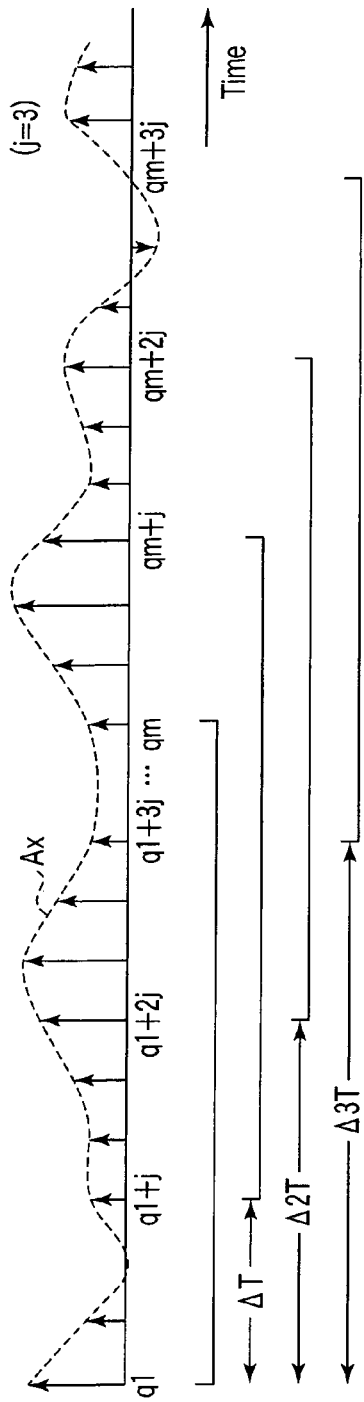
FIGS. 4A and 4B are graphs showing a method of calculating a Doppler spectrum in the first embodiment.
Figure 4B:
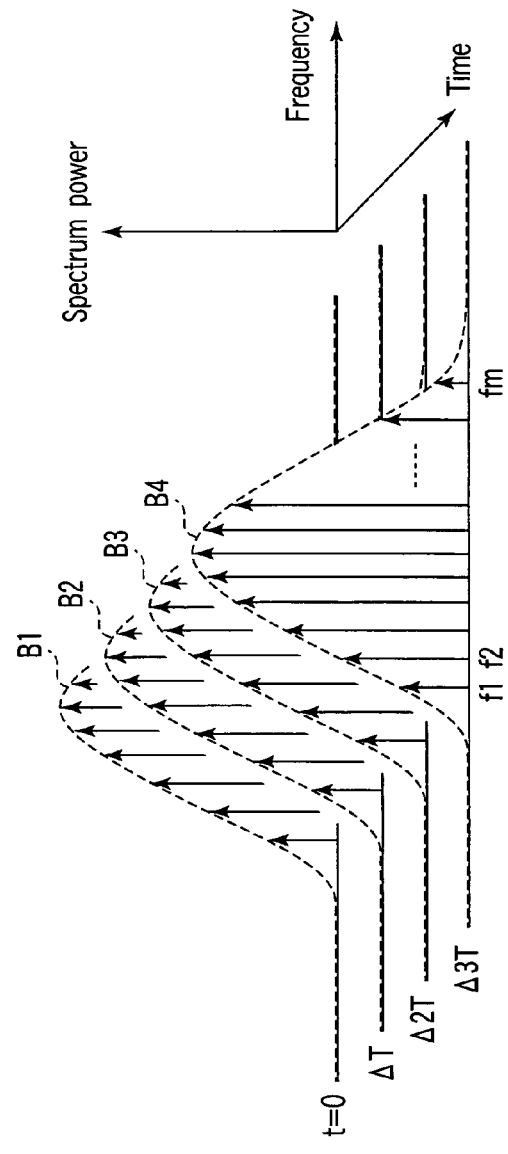

FIGS. 4A and 4B show a method of calculating a Doppler spectrum by using the FFT analyzer 443. FIG. 4A shows a Doppler signal Ax input to the FFT analyzer 443. FIG. 4B shows Doppler spectrum data B1, B2, B3, . . . obtained by performing FFT analysis in a predetermined period of the Doppler signal Ax. The first Doppler spectrum B1 corresponding to spectrum components f1 to fm is calculated by performing FFT analysis for m Doppler signal components q1 to qm of the discrete Doppler signal (FIG. 4A) supplied from the HPF 442. The new Doppler spectrum data B2 is calculated by FFT analysis for m Doppler signal components q1+j to qm+j after a time ΔT. Note that FIG. 4A shows a case wherein j=3.

Subsequently, likewise, the Doppler spectra B3, B4, . . . corresponding to spectrum components f1 to fm are generated by sequentially performing FFT analysis for m Doppler signal components q1+2j to qm+2j after a time 2ΔT, q1+3j to qm+3j after a time 3ΔT, . . . (FIG. 4B).

Referring back to FIG. 1, the blood flow evaluating unit 6 comprises a trace waveform generating unit 61 which generates the trace waveform of the maximum blood flow velocity Vp corresponding to a maximum frequency fp of a plurality of Doppler spectra time-serially obtained by the spectrum calculating unit 44, a local maximum/minimum detecting unit 62 which detects a local maximum/minimum pair with respect to this trace waveform, and a cardiac cycle setting unit 63 which sets a cardiac cycle on the basis of the heartbeat information of the object which is supplied from the living body measuring unit 9. The blood flow evaluating unit 6 further comprises a feature amount selecting unit 64 which selects E and A waves as feature amounts of a trace waveform in left ventricular blood inflow measurement from a plurality of local maximum/minimum pairs in the set cardiac cycle on the basis of a selection criterion set in advance, and a diagnostic parameter measuring unit 65 which measures various kinds of diagnostic parameters on the basis of the amplitudes or waveforms of the selected E and A waves.

Figure 5:
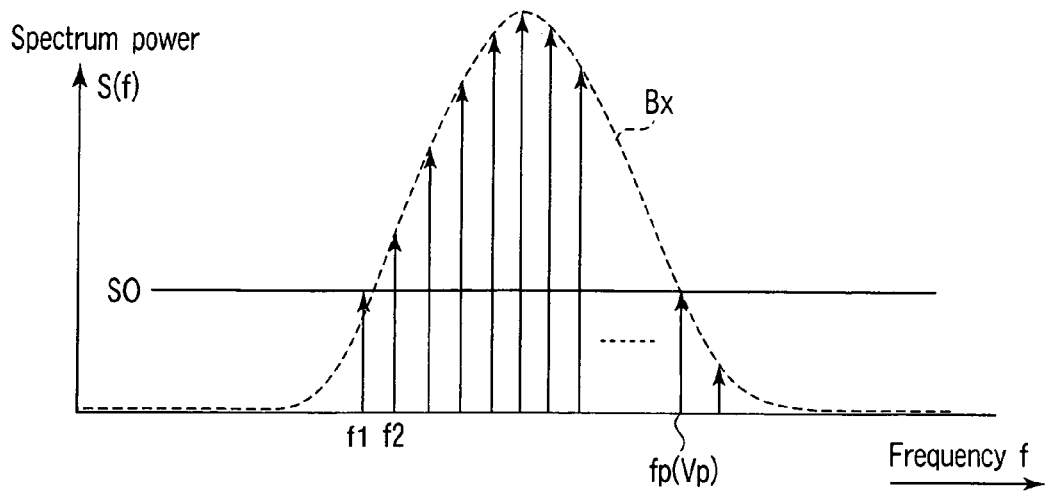
FIG. 5 is a graph showing a method of calculating the maximum frequency component of a Doppler spectrum in the first embodiment.

The trace waveform generating unit 61 detects the maximum frequency fp with respect to a plurality of Doppler spectra B1, B2, B3, . . . obtained by the spectrum calculating unit 44 at ΔT intervals, and generates a trace waveform representing a temporal change in the maximum blood flow velocity Vp corresponding to the maximum frequency fp. FIG. 5 shows a method of calculating the above maximum frequency fp. The maximum frequency fp is obtained on the basis of the intersection between a preset spectrum threshold S0 and a Doppler spectrum Bx.

In the following description, the maximum blood flow velocity Vp corresponding to the maximum frequency fp of the Doppler spectrum is called the maximum blood flow velocity Vp of the Doppler spectrum. A case wherein various kinds of diagnostic parameters are measured on the basis of the trace waveform of the maximum blood flow velocity Vp will be described below.

Figure 6A:
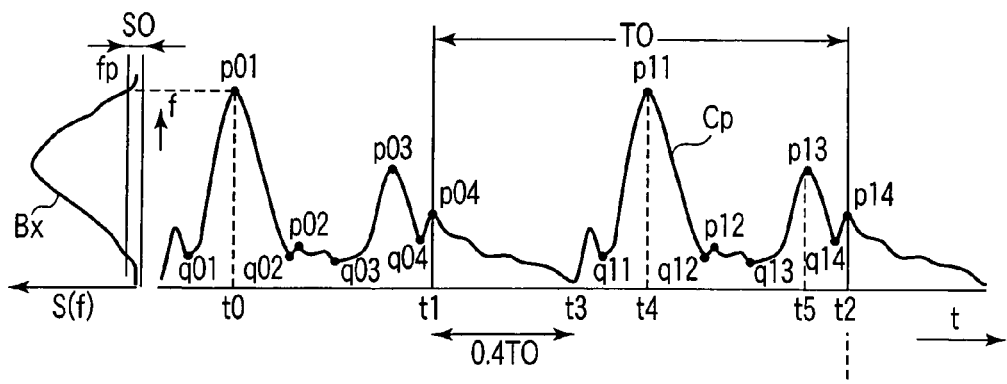
FIGS. 6A and 6B are graphs showing a trace waveform in left ventricular blood inflow measurement in the first embodiment.
Figure 6B:
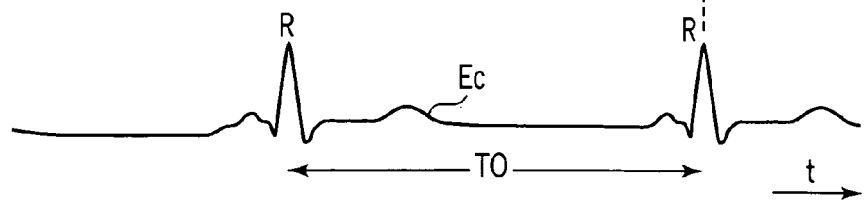

The local maximum/minimum detecting unit 62 of the blood flow evaluating unit 6 detects a local maximum/minimum pair corresponding to the trace waveform of the maximum blood flow velocity Vp generated by the trace waveform generating unit 61. FIG. 6A shows the trace waveform of the maximum blood flow velocity Vp generated by the trace waveform generating unit 61 on the basis of the Doppler spectrum of a cardiac left ventricular blood inflow which is obtained by setting a range gate in the mitral valve outflow portion of the object. The left end portion of this graph shows a Doppler spectrum Bx at time t=t0. In addition, the graph shows a trace waveform Cp indicating a temporal change in the maximum blood flow velocity Vp measured in the Doppler spectrum Bx.

The local maximum/minimum detecting unit 62 detects a plurality of local maximum/minimum pairs by performing gradient operation and Laplacian operation for inflection point detection with respect to the trace waveform Cp generated by the trace waveform generating unit 61. That is, as indicated by the trace waveform Cp in FIG. 6A, local maximum/minimum pairs [p01, q01], [p01, q01], [p03, q03], . . . are detected.

The cardiac cycle setting unit 63 sets a cardiac cycle on the basis of the heartbeat information of the object which is supplied from the living body measuring unit 9. For example, the cardiac cycle setting unit 63 detects the position of an R wave by detecting the maximum value of an ECG waveform in FIG. 6B which is supplied from an ECG unit (electrocardiograph) of the living body measuring unit 9, and sets a cardiac cycle T0 in accordance with an R-R interval.

The feature amount selecting unit 64 comprises a storage circuit (not shown). In this storage circuit, a selection criterion for the selection of an E wave (early diastoric flow) and A wave (atrial contraction flow) from a plurality of local maximum/minimum pairs set in a trace waveform is stored in advance as database data. FIG. 7 schematically shows a selection criterion database stored in the storage circuit, in which the selection criteria are set in correspondence with different measurement targets of objects to be examined and different age groups.

For example, in a database DB1, a selection criterion for E and A waves with respect to a trace waveform obtained in left ventricular blood inflow measurement of adults (elderly) is stored. In a database DB2, a selection criterion for S, D, and AR waves with respect to a trace waveform obtained in pulmonary artery blood flow measurement is stored.

In addition, the selection criteria stored in the database DB1 include selection criteria for automatically selecting various kinds of waveforms on the basis of cardiac cycles set in accordance with an ECG waveform, a PCG (phonocardiographic) waveform, and the trace waveform shown in FIG. 6A as trigger waveforms, and selection criteria for automatic selection on the basis of manually set cardiac cycles or heartbeat triggers.

The feature amount selecting unit 64 receives the trace waveform Cp (FIG. 6A) to which the information of the local maximum/minimum pair is added from the local maximum/minimum detecting unit 62, and the cardiac cycle information (FIG. 6B) from the cardiac cycle setting unit 63, and sets the cardiac cycle T0 with respect to the trace waveform Cp in an interval [t1-t2]. The feature amount selecting unit 64 detects local maximum/minimum pairs [p11, q11], [p12, q12], [p13, q13], . . . which have already been set in the trace waveform Cp with reference to time t3, at which 40% of the cardiac cycle T0 has elapsed from the R wave of the ECG waveform at time t1, up to time t2, and detects the local maximums p11 and p13 respectively having the maximum value and the second local maximum value.

Subsequently, of the two local maximum values p11 and p13, the local maximum p11 at time t4 near time t3 is selected as an E wave, and the local maximum p13 at time t5 following the local maximum p11 is selected as an A wave. Position (time) information t4 of the selected E wave and position information t5 of the A wave are supplied to the diagnostic parameter measuring unit 65.

The diagnostic parameter measuring unit 65 comprises a computing circuit (not shown), and measures diagnostic parameters "E/A" and "DCT (deceleration time)" on the basis of the trace waveform Cp of the maximum blood flow velocity Vp, the position information t4 of the E wave, and the position information t5 of the A wave supplied from the feature amount selecting unit 64.

A measuring method of diagnostic parameter performed by the diagnostic parameter measuring unit 65 with respect to the trace waveform Cp will be described with reference to FIGS. 9A and 9B. The computing circuit of the diagnostic parameter measuring unit 65 calculates the diagnostic parameter "E/A" in accordance with a ratio VE/VA between an amplitude (flow velocity) VE of the E wave of the trace waveform Cp at time t4 and an amplitude (flow velocity) VA of the A wave at time t5. A tangent Ct is set with respect to a descending curve from the local maximum p11 of the E wave, and the interval between time t6, at which the tangent Ct crosses a baseline B1, and time t4 of the E wave is calculated as the diagnostic parameter "DCT".

The data storage unit 5 in FIG. 1 then stores the B mode image data and color Doppler image data generated by the data generating unit 4 and Doppler spectrum data generated by combining a plurality of Doppler spectra. The data storage unit 5 further stores the trace waveform generated by the trace waveform generating unit 61 of the blood flow evaluating unit 6 on the basis of a Doppler spectrum, the information of the E and A waves selected by the feature amount selecting unit 64 in a predetermined cardiac cycle of this trace waveform, and the measurement results on the diagnostic parameters "E/A" and "DCT" measured by the diagnostic parameter measuring unit 65 in the predetermined cardiac cycle.

The display unit 7 comprises a display data generating circuit, conversion circuit, and monitor which are not shown. The B mode image data, color Doppler image data, and Doppler spectrum data generated by the data generating unit 4 and the like, the trace waveform of the maximum blood flow velocity Vp obtained by the blood flow evaluating unit 6, and the measurement results on the diagnostic parameters "E/A" and "DCT" are combined and converted into data in a predetermined display format by the display data generating circuit. The resultant data is then subjected to D/A conversion and TV format conversion in the conversion circuit to be displayed on the monitor.

FIG. 10 shows a specific example of a display method for the monitor of the display unit 7. The following areas are provided on the monitor: an image data display area 200 on which B mode image data and color Doppler image data are combined and displayed; a trace waveform display area 300 on which a trace waveform and ECG waveform superimposed on Doppler spectrum data (not shown) are displayed; and a diagnostic parameter display area 400 on which a list of the measurement values of diagnostic parameters such as "E/A" and "DCT" is displayed.

A Doppler marker 201 and range gate position 202 are displayed on a B mode image and color Doppler image displayed on the image data display area 200. The Doppler marker 201 indicates the direction of a region of interest for the acquisition of a Doppler spectrum. The range gate position 202 is set in a region of interest (e.g., a mitral valve outflow portion) on the Doppler marker 201. The position information and amplitude information of E and A waves, the tangent Ct for the measurement of the diagnostic parameter "DCT", and the like are superimposed and displayed on the trace waveform Cp in the trace waveform display area 300.

The input unit 8 comprises input devices such as a display panel on an operation panel, a keyboard, a trackball, a mouse, and selection buttons, and is used to input patient information, select an image display mode and display method, select a measurement mode and trigger waveform, set ultrasonic data acquisition conditions, and input various kinds of command signals.

The above image display mode includes a B mode, color Doppler mode, and Doppler spectrum mode. The measurement mode includes left ventricular blood inflow measurement, pulmonary artery blood flow measurement, and the like using the trace waveform of Doppler spectrum data. The trigger waveform includes an ECG waveform, PCG waveform, Vp trace waveform, and the like as shown in FIG. 5 or 6. The display method includes, for example, real-time display and freeze display of image data, trace waveforms, and diagnostic parameter measurement values. In addition, manual scrolling of a trace waveform in freeze display, setting of the positions of a Doppler marker and range gate for the acquisition of a Doppler spectrum, and the like are also performed by using the input device of the input unit 8.

The system control unit 10 comprises a CPU and storage circuit (not shown). The input information, setting information, and selection information input by the operator in advance from the input unit 8 are stored in the storage circuit. The CPU systematically controls the respective units of the ultrasonic Doppler diagnostic apparatus 100 and the overall system on the basis of the above information input from the input unit 8.

The living body measuring unit 9 acquires the heartbeat information of an object to be examined. This embodiment will exemplifies the case wherein an ECG unit which acquires an ECG waveform from an object to be examined is used. However, another kind of living body signal measuring unit such as a PCG unit or the like which acquires a phonocardiographic wave (PCG waveform) may be used.

(Diagnostic Parameter Measurement Sequence)

A diagnostic parameter measurement sequence in this embodiment will be described next with reference to FIGS. 1 to 11. FIG. 11 is a flowchart showing a sequence for measuring diagnostic parameters in this embodiment.

The following description will be made about a sequence for measuring the diagnostic parameters "E/A" and "DCT" by selecting E and A waves with respect to the trace waveform Cp of the maximum blood flow velocity Vp generated with respect to the Doppler spectrum of a left ventricular blood inflow on the basis of heartbeat information obtained from an ECG waveform. However, the measurement target, trigger waveform, diagnostic parameters, and the like to be used are not limited to them.

Prior to the transmission/reception of ultrasonic waves with respect to an object to be examined, an operator operates the input unit 8 to input patient information, select an image display mode, measurement mode, and trigger waveform, and set and update various kinds of ultrasonic data acquisition conditions. These pieces of information are stored in the storage circuit (not shown) of the system control unit 10.

In this embodiment, the operator selects the B mode, color Doppler mode, and Doppler spectrum mode as image display modes, and selects left ventricular blood inflow measurement based on the trace waveform Cp of the maximum blood flow velocity Vp as a measurement mode. The operator further selects an ECG waveform as a trigger waveform used for the selection of E and A waves of a trace waveform in this left ventricular blood inflow measurement, and selects real-time display as a display method for a trace waveform and diagnostic parameter measurement results (step S1 in FIG. 11).

When these inputting/selecting/setting operations are complete, the operator fixes the distal end (ultrasonic wave transmission/reception surface) of the ultrasonic probe 3 at a predetermined position on the body surface of the object. Ultrasonic wave transmission/reception is then performed in the first ultrasonic wave transmission/reception direction (scanning direction θ1) to obtain B mode data and color Doppler data. That is, the rate pulse generator 211 in the transmission/reception unit 2 in FIG. 2 frequency-divides the reference signal supplied from the reference signal generating unit 1 to generate a rate pulse for determining the repetition period of ultrasonic pulses applied into the object, and supplies the rate pulse to the transmission delay circuit 212.

The transmission delay circuit 212 gives the rate pulse a focusing delay time for the focusing of ultrasonic waves to a predetermined depth and a deflection delay time for the transmission of ultrasonic waves in the scanning direction θ1, and supplies the resultant rate pulse to the pulser 213. The pulser 213 then supplies driving signals generated by the rate pulse to the N piezoelectric transducers of the ultrasonic probe 3 through a cable (not shown) to apply ultrasonic pulses in the scanning direction θ1 of the object.

The ultrasonic pulses applied to the object are partially reflected by the boundary surfaces between organs having different acoustic impedances or tissues in the organs. When such ultrasonic waves are reflected by a moving reflector such as the cardiac wall and blood cells, the ultrasonic frequency is Doppler-shifted.

The reflected ultrasonic waves (reception ultrasonic waves) reflected by tissue or blood cells in the object are received by the piezoelectric transducers of the ultrasonic probe 3 to be converted into electrical signals (reception signals). The reception signals are converted into digital signals by the A/D converter 222 after being amplified to a predetermined magnitude by the independent N-channel preamplifier 221 in the reception unit 22. The beam former 223 gives the reception signals converted into the digital signals predetermined delay times. The resultant signals are added/combined by the adder 224. The resultant signal is then supplied to the B mode data generating unit 41 and Doppler signal detecting unit 42 of the data generating unit 4.

At this time, in the beam former 223, a delay time for the focusing of reflected ultrasonic waves from a predetermined depth and a delay time for the acquisition of strong reception directivity in the scanning direction θ1 with respect to reflected ultrasonic waves are set in accordance with control signals from the system control unit 10.

The output signal from the adder 224 which is supplied to the B mode data generating unit 41 is subjected to envelope detection and logarithmic conversion. The resultant signal is then stored in the B mode image data storage area in the data storage unit 5 in FIG. 1.

In generating color Doppler image data, ultrasonic wave transmission/reception is consecutively performed a plurality of number of times (L times) in the scanning direction θ1 by the same sequence as that for the acquisition of a Doppler shift of a reception signal, and autocorrelation computation is performed for the resultant reception signal.

The reception signal obtained by the first ultrasonic wave transmission/reception for color Doppler data in the scanning direction θ1 which is performed by the transmission/reception unit 2 is supplied from the adder 224 to the Doppler signal detecting unit 42. The mixers 422-1 and 422-2 and the LPFs 423-1 and 423-2 detect a 2-channel Doppler signal (complex signal) by quadrature phase detection. The real and imaginary components of this Doppler signal are temporarily stored in the Doppler signal storage circuit 431 of the color Doppler data generating unit 43. Doppler signals are acquired by performing the same processing for reception signals obtained by the second ultrasonic wave transmission/reception to the Lth ultrasonic wave transmission/reception in the scanning direction θ1. The signals are then stored in the Doppler signal storage circuit 431.

Upon completing the storage of the Doppler signals obtained by L times of ultrasonic wave transmission in the scanning direction θ1 in the Doppler signal storage circuit 431, the system control unit 10 sequentially reads out Doppler signal components corresponding to a predetermined position (depth) from the Doppler signals stored in the Doppler signal storage circuit 431, and supplies them to the MTI filter 432. The MTI filter 432 filters the supplied Doppler signal components to remove tissue Doppler components (clutter components) caused by the motion of tissue such as cardiac muscle, and supplies the Doppler signal constituted by the blood flow Doppler components due to the blood flow to the autocorrelation computing unit 433.

The autocorrelation computing unit 433 performs autocorrelation computation by using the Doppler signal supplied from the MTI filter 432, and calculates an average flow velocity value, variance, power value, or the like on the basis of the autocorrelation computation result. Such computation is performed with respect to other positions (depths) in the scanning direction θ1, and the calculated average blood flow velocity, variance, power value, or the like in the scanning direction θ1 is stored in the color Doppler image data storage area in the data storage unit 5 in FIG. 1.

The system control unit 10 performs ultrasonic wave transmission/reception in scanning directions θ2 to θP according to the same sequence. The B mode data and color Doppler data obtained at this time are stored in the B mode image data storage area and color Doppler image data storage area in the data storage unit 5.

That is, the B mode data corresponding to the scanning directions θ1 to θP are sequentially stored in the B mode image data storage area in the data storage unit 5 to generate B mode image data corresponding to one frame. Likewise, the color Doppler image data corresponding to the scanning directions θ1 to θP are stored in the color Doppler image data storage area to generate color Doppler image data corresponding to one frame.

The display data generating circuit of the display unit 7 combines the 1-frame image data stored in the data storage unit 5, i.e., the B mode image data obtained in the scanning directions θ1 to θP, and the color Doppler image data, and converts the resultant data into data in a predetermined display format. The conversion circuit performs D/A conversion and TV format conversion of the combined image data, thereby generating a video signal. The obtained video signal is displayed on the monitor.

Subsequently, ultrasonic wave transmission/reception is repeated in the directions θ1 to θP in the same manner as described above, and the resultant B mode image data and color Doppler image data are displayed on the display unit 7 in real time.

The operator then uses an input device of the input unit 8 to set a Doppler marker in a direction θD to set a diagnosis region (mitral valve) for a Doppler spectrum with respect to the B mode image or color Doppler image of the object displayed on the monitor of the display unit 7. The range gate is set at the distance Lg on this Doppler maker.

B mode or color Doppler ultrasonic wave transmission/reception repetitively performed in the scanning directions θ1 to θP and ultrasonic wave transmission/reception for the acquisition of a Doppler spectrum in the scanning direction θD corresponding to the Doppler marker are alternately performed. In this case as well, ultrasonic wave transmission/reception is performed in the direction θD by the same sequence as that for color Doppler ultrasonic wave transmission/reception. The output signal (reception signal) from the adder 224 is supplied to the Doppler signal detecting unit 42.

As described above with reference to FIG. 3, the Doppler signal detecting unit 42 supplies the Doppler signal detected by quadrature phase detection of the reception signal to the SH 441 of the spectrum calculating unit 44 (step S2 in FIG. 11). The SH 441 samples/holds the Doppler signal on the basis of a sampling pulse at the range gate position Lg which is supplied from the system control unit 10.

The output from the SH 441, which is obtained by repetitive ultrasonic wave transmission/reception in the scanning direction θD, is smoothed by the HPF 442 and stored in the storage circuit (not shown) of the FFT analyzer 443.

The computing circuit (not shown) of the FFT analyzer 443 sets a plurality of periods shifted by a predetermined time ΔT from each other with respect to continuously obtained Doppler signals, and generates a Doppler spectrum by performing FFT analysis for the Doppler signal in each of the periods.

That is, as shown in FIG. 4A, the computing circuit of the FFT analyzer 443 calculates a Doppler spectrum B1 corresponding to frequencies f1 to fm by performing FFT analysis for discretely supplied Doppler signals by reading out, for example, m signal components q1 to qm. The calculated Doppler spectrum B1 is stored in a Doppler spectrum data storage area in the data storage unit 5.

In the same manner, the FFT analyzer 443 of the spectrum data calculating unit 44 calculates Doppler spectra B2, B3, B4, . . . with respect to m signal components after the times ΔT, 2ΔT, 3ΔT, . . . . The calculated Doppler spectra are then sequentially stored in the Doppler spectrum data storage area in the data storage unit 5 (step S3 in FIG. 11).

The trace waveform generating unit 61 of the blood flow evaluating unit 6 sequentially reads out the Doppler spectra B1, B2, B3, . . . stored in the data storage unit 5, and calculates the maximum frequency fp of each Doppler spectrum by the method shown in FIG. 5. The trace waveform generating unit 61 then generates the trace waveform Cp representing a temporal change in the maximum blood flow velocity Vp corresponding to the maximum frequency fp and stores it in the trace waveform storage area in the data storage unit 5 (step S4 in FIG. 11).

Subsequently, the local maximum/minimum detecting unit 62 reads out the trace waveform data Cp stored in the data storage unit 5, and detects local maximum/minimum pairs [p01, q01], [p02, q02], [p03, q03], . . . by performing gradient operation and Laplacian operation for the trace waveform Cp (see FIG. 6A). The trace waveform data Cp to which these local maximum/minimum pairs are added is stored in the trace waveform storage area in the data storage unit 5 and supplied to the feature amount selecting unit 64 (step S5 in FIG. 11).

The cardiac cycle setting unit 63 detects an R wave by detecting the maximum value of an ECG waveform supplied from the living body measuring unit 9 having an ECG unit, and supplies the cardiac cycle information set in accordance with the R-R interval to the feature amount selecting unit 64.

The feature amount selecting unit 64 sets one cardiac period T0 with respect to the trace waveform supplied from the local maximum/minimum detecting unit 62 on the basis of the cardiac cycle information supplied from the cardiac cycle setting unit 63, and selects E and A waves by applying a preset waveform selection criterion to a plurality of local maximum/minimum pairs added to the trace waveform in the cardiac period T0. The feature amount selecting unit 64 then supplies the position information of the selected E wave and the position information of the selected A wave to the diagnostic parameter measuring unit 65, together with the trace waveform Cp described above (step S6 in FIG. 11).

The diagnostic parameter measuring unit 65 of the blood flow evaluating unit 6 measures an amplitude VE of the E wave and an amplitude VA of the A wave of the trace waveform Cp on the basis of the position information of the E and A waves supplied from the feature amount selecting unit 64, and calculates the diagnostic parameter "E/A" in accordance with a ratio VE/VA. As shown in FIG. 9B, the diagnostic parameter measuring unit 65 further sets the tangent Ct with respect to a descending curve from the local maximum of the E wave, and calculates the interval between the position (time) of intersection between the tangent Ct and the baseline B1 and the position (time) of the E wave as the diagnostic parameter "DCT" (step S7 in FIG. 11). The diagnostic parameters "E/A" and "DCT" calculated in this manner are stored in the data storage unit 5.

The B mode image data, the color Doppler image data, the Doppler spectrum data, the trace waveform Cp of the maximum blood flow velocity Vp to which the information of the E and A waves is added, and the measurement results on the diagnostic parameters "E/A" and "DCT" which are stored in the data storage unit 5 according to the above sequence are supplied to the display unit 7. These data are combined by the display data generating circuit and converted in accordance with a predetermined display format. The resultant data is subjected to D/A conversion and TV format conversion in the conversion circuit and is displayed on the monitor.

For example, as shown in FIG. 10, the B mode image data stored in the B mode image data storage area in the data storage unit 5 and the color Doppler image data stored in the color Doppler image data storage area are combined and displayed in the image data display area 200 on the monitor.

In addition, Doppler spectrum image data (not shown) is displayed in the trace waveform display area 300, while the trace waveform Cp, markers or cursors indicating the positions of the E and A waves, the tangent Ct from the local maximum of the E wave, and the like are superimposed on the image data. Furthermore, the diagnostic parameters "E/A" and "DCT" are displayed in the diagnostic parameter display area 400 (step S8 in FIG. 11).

The respective units of the blood flow evaluating unit 6 generate a trace waveform, detect a local maximum/minimum pair, select E and A waves in the latest cardiac cycle, and measure diagnostic parameters with respect to Doppler spectra continuously obtained at the range gate positions set in the B mode image data and color Doppler image data displayed on the display unit 7 in real time according to the above sequence.

The obtained B mode image data and color Doppler image data, and the Doppler spectrum data and trace waveform are sequentially displayed in the image data display area 200 and trace waveform display area 300 in real time, respectively. In addition, the latest measurement results on the diagnostic parameters "E/A" and "DCT" measured by the diagnostic parameter measuring unit 65 on the basis of the E and A waves of the trace waveform in the latest cardiac cycle selected by the feature amount selecting unit 64 of the blood flow evaluating unit 6 are displayed in the diagnostic parameter display area 400. In this case, it is preferable that the trace waveform in the cardiac cycle corresponding to the latest measurement results on the diagnostic parameters be highlighted or a marker or cursor be superimposed/displayed on the trace waveform so as to be emphasized.

As described above, according to this embodiment, when various kinds of diagnostic parameters are to be measured to perform cardiac function measurement on the basis of the trace waveform of a Doppler spectrum, since E and A waves and the like required for this measurement are selected on the basis of a selection criterion as database data, accurate waveform selection can be performed. This therefore makes it possible to improve the measurement accuracy of diagnostic parameters.

The above waveform selection requires no manual operation by the operator, and hence the time required to measure diagnostic parameters is shortened, and measurement results can be displayed in real time. This greatly improves the measurement efficiency and diagnosis efficiency.

In addition, since the measurement of diagnostic parameters in this embodiment requires no manual operation by the operator, measurement results do not depend on the experience of an operator. Therefore, measurement results with excellent reproducibility can be easily obtained.

Furthermore, since a predetermined period of a trace waveform corresponding to a measurement result on a diagnostic parameter displayed on the display unit is explicitly indicated, the reliability of the measurement result on the diagnostic parameter can be checked by using the trace waveform.

(Second Embodiment)

The second embodiment of the present invention will be described next. An ultrasonic Doppler diagnostic apparatus according to this embodiment executes CAB (Cut and Arraign by Beat) processing by using a trace waveform obtained by auto-trace processing and analyzes the result, thereby providing information which can support diagnosis.

Figure 15:
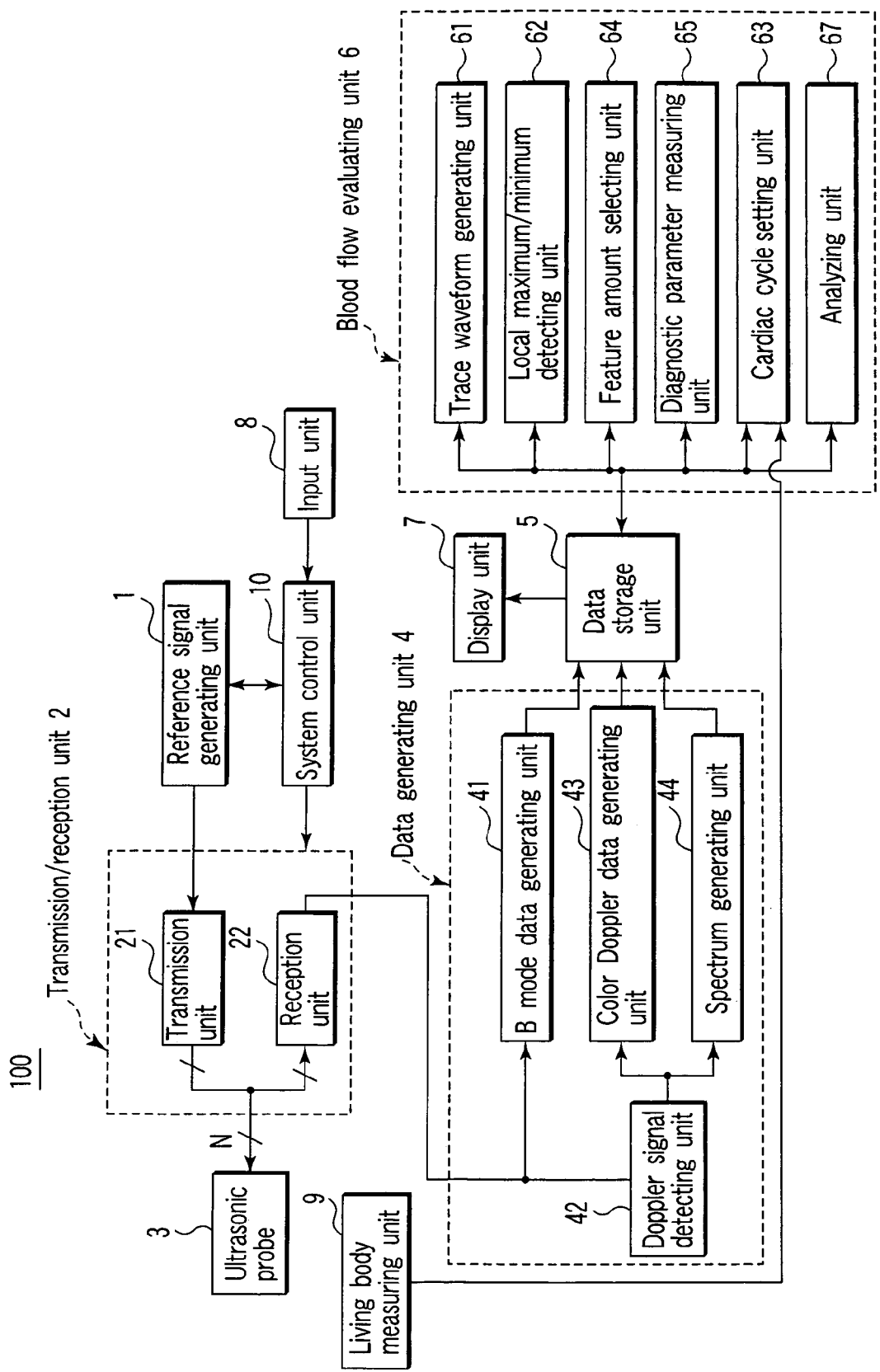
FIG. 15 is a block diagram showing the arrangement of an ultrasonic Doppler diagnostic apparatus according to the second embodiment.

FIG. 15 is a block diagram showing the arrangement of the ultrasonic Doppler diagnostic apparatus according to this embodiment. Only different points from the ultrasonic Doppler diagnostic apparatus according to the first embodiment will be described below.

A feature amount selecting unit 64 executes CAB processing (processing conforming to a CAB function to be described later) for the trace waveforms of Vp, Vc, and the like which are generated by a trace waveform generating unit 61. The feature amount selecting unit 64 also generates a diagnostic waveform by performing statistical processing using a trace waveform for each cardiac cycle which is obtained by CAB processing.

A diagnostic parameter measuring unit 65 measures a diagnostic parameter by using a generated diagnostic waveform.

An analyzing unit 67 analyzes a measurement result on a diagnostic parameter and a diagnostic waveform by using a diagnostic database stored in advance to determine whether a diagnosis target region is normal or abnormal.

A display unit 7 displays a trace waveform for each cardiac cycle which is obtained by CAB processing, a measurement result on a diagnostic parameter using a diagnostic waveform, a determination result indicating whether a diagnosis target region is normal or abnormal, and the like in a predetermined form.

(CAB Function)

The CAB function of the ultrasonic Doppler diagnostic apparatus according to this embodiment will be described next. The CAB function serves to extract a trace waveform obtained by auto-trace processing for each heartbeat with reference to a predetermined time phase and array the extracted waveforms in a coordinate system defined by the first time axis (the time direction associated with a heart rate) and the second time axis (the time direction in one cardiac cycle).

Figure 16:
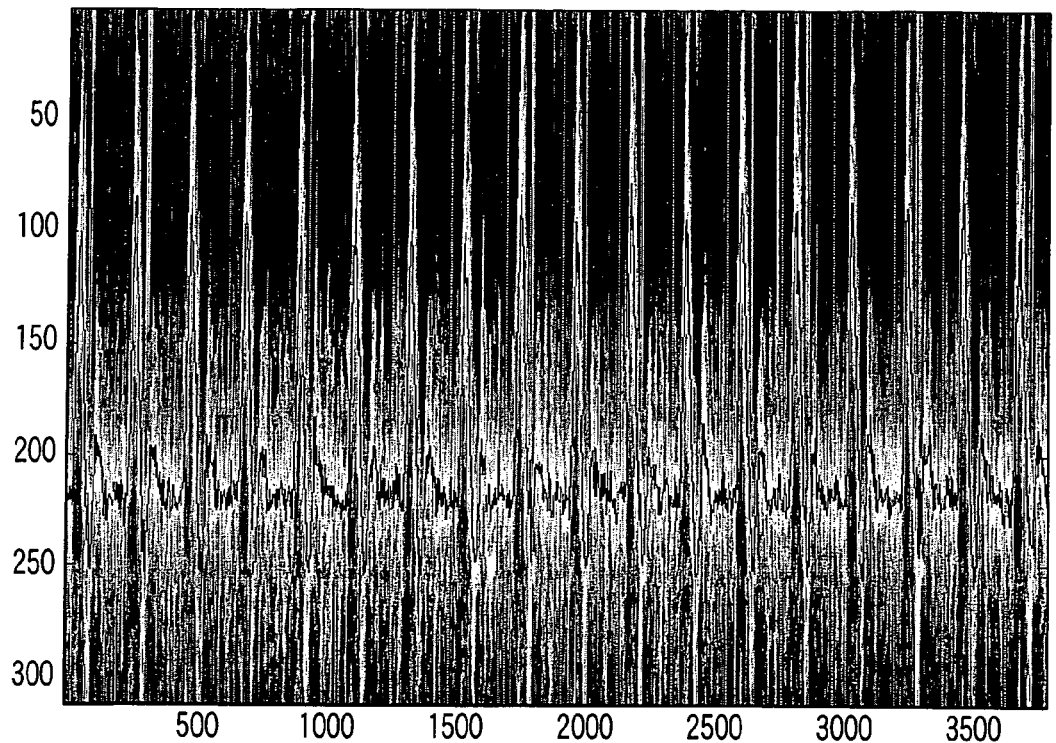
FIG. 16 is a chart showing a trace waveform representing a temporal change in a maximum blood flow velocity Vp which is obtained on the basis of a spectrum waveform (corresponding to 18 heartbeats) in the carotid.
Figure 17:
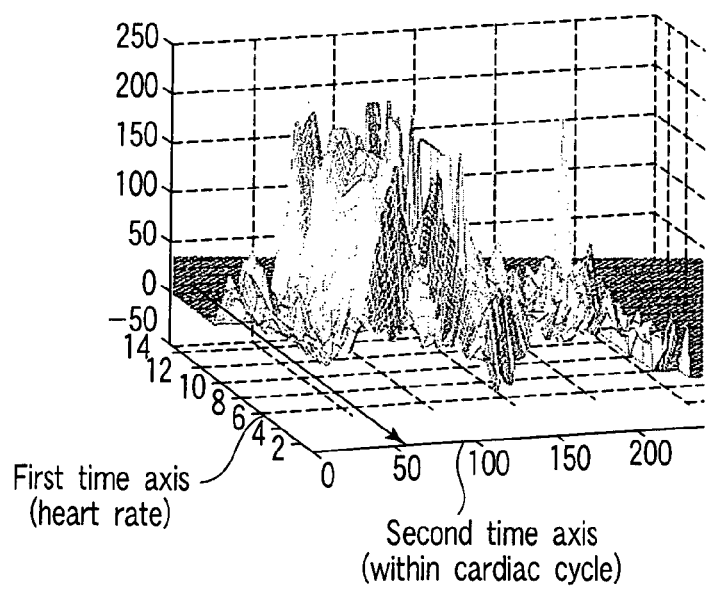
FIG. 17 is a chart showing a result obtained by CAB processing in which a trace waveform of a Vp waveform is input.
Figure 18:
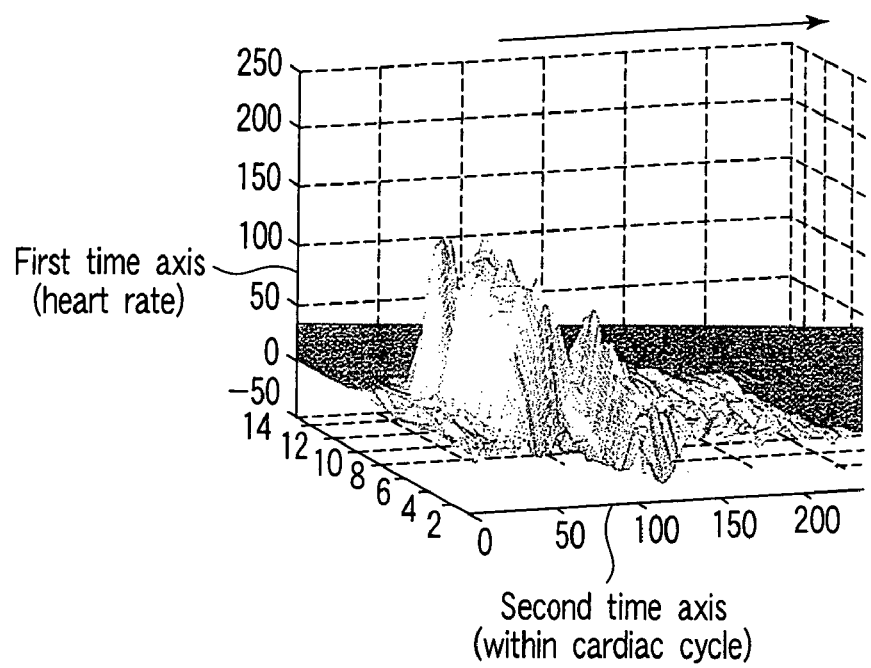
FIG. 18 is a chart showing a result obtained by CAB processing in which a trace waveform of a Vc waveform is input.

FIG. 16 is a graph showing a trace waveform representing a temporal change in the maximum blood flow velocity Vp which is obtained on the basis of the spectrum waveform (corresponding to 18 heartbeats) obtained from the carotid. Upon receiving this trace waveform, the feature amount selecting unit 64 detects all ED positions (or PS positions or the like) on the trace waveform in accordance with an ECG waveform from the cardiac cycle setting unit 63. In addition, the feature amount selecting unit 64 extracts a trace waveform for each cardiac cycle with reference to each detected ED position or the like, and arrays the extracted waveforms in the coordinate system defined by the time axis associated with amplitude and heart rate and the time axis in one cardiac cycle, thereby generating CAB data, as shown in FIG. 17. The generated CAB data is displayed on the display unit 7, together with the trace waveform, as needed. FIG. 18 shows CAB data obtained by CAB processing upon receiving the trace waveform of the Vc waveform.

(Diagnostic Parameter Measuring Function Using CAB Data)

Figure 19:
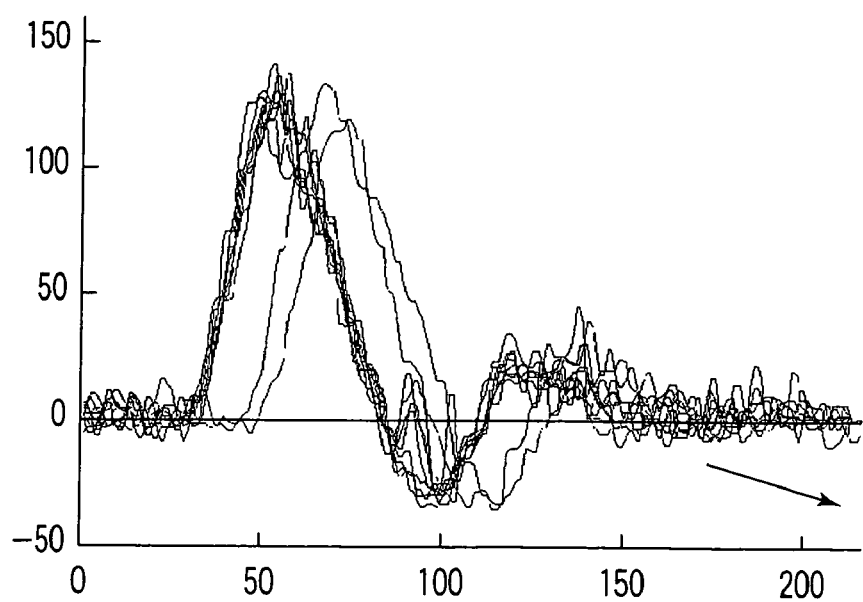
FIG. 19 is a chart two-dimensionally showing CAB data obtained by CAB processing.

The diagnostic parameter measuring function of the ultrasonic Doppler diagnostic apparatus according to this embodiment which uses CAB data will be described next. This function serves to generate a diagnostic waveform by performing statistical processing using CAB data obtained by CAB processing shown in FIG. 19 (which is two-dimensional display). Statistical processing which can be used includes, for example, multiple heartbeat averaging processing, AR (Auto-Regressive) time axis model calculation processing, ARX (Auto-Regressive and exogenious) time axis model calculation processing, and the like.

Multiple heartbeat averaging processing is executed according to $$x(n) = \frac{1}{N} * \sum_{k=1}^{N} CAB(x(n), k) \qquad (1)$$

where N is a multiple heartbeat heart rate (N=18 in this case), which corresponds to a parameter for averaging calculation, CAB (x, y) is the amplitude of each trace waveform extracted by CAB processing, x is the time associated with a heart rate, and y is the time in one cardiac cycle.

AR time axis model calculation processing is executed by using a general method such as the Burg (MEM) method, geometric lattice method, Yule-Walker method, or modified covariance method according to $$x(n) = \sum_{i=1}^{k} \alpha i * x(n-i) + u(n) \qquad (2)$$

where X(n) is trace waveform data, u(n) is a residual, αi is an AR coefficient sequence, and k is a model degree. The observation time for X(n) varies depending on parameters for averaging processing and the like.

ARX time axis model calculation processing is a mathematical model which uses an ECG waveform as an exogenous input and makes a trace waveform autoregressive. This processing is executed according to $$A(q)*y(k)=B(q)*U(k)+w(k) \qquad (3)$$

FIG. 20 shows an example of a diagnostic waveform (predictive waveform) obtained by ARX time axis model calculation processing.

The feature amount selecting unit 64 selects a feature amount by using the diagnostic waveform generated by the statistical processing exemplified above and the technique described in the first embodiment. When, for example, a blood flow velocity in each cardiac apex and a valve velocity are expressed by auto-trace waveforms, blood flow and valve peak velocities are selected by using the generated diagnostic waveforms. The diagnostic parameter measuring unit 65 measures diagnostic parameters, the ratio between the maximum value of Ve and the maximum value of Vma of the mitral valve, and the time interval between an E wave and an A wave, described in the first embodiment, in a Tei-index manner.

(Frequency Parametric Model)

A frequency parametric model can also be used. According to the frequency parametric model shown in FIG. 21, an AR model is obtained by using equation (4), and is expanded by using equation (5).

$$A(0)*y(n) + A(1)*y(n-1) + \cdots + A(q)*y(n-q) = e(n) \qquad (4)$$

$$P(f) = PT \bigg/ \bigg[1 + \sum_{}^{q} A(q)*\exp(-j \cdot 2\pi \cdot f \cdot q)\bigg]^2 \qquad (5)$$

where e(n) is noise, y(n) is an output, and A( ) is an AR model of a coefficient sequence. In addition, PT in equation (5) can be expressed as follows to normalize P(f):

$$PT = R(0) + \sum_{}^{q} A(q) \cdot R(k-q) \qquad (6)$$

where R is a cofraction. The frequency model P(f) can be calculated by the above technique.

(Diagnosis Support Function Using CAB Data)

The diagnosis support function of the ultrasonic Doppler diagnostic apparatus according to this embodiment which uses CAB data will be described next. The diagnosis support function using CAB data serves to perform analysis using at least one of the diagnostic waveform and diagnostic parameter obtained by the diagnostic parameter measuring function and determine on the basis of the analysis result whether a diagnosis target region is normal or abnormal.

Figure 22:
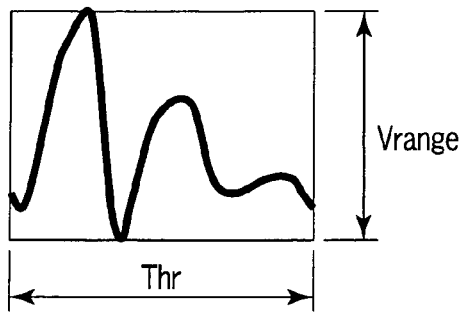
FIG. 22 is a graph showing an example of a reference waveform to be stored as a normal model for each age and each diagnosis region.
Figure 23:
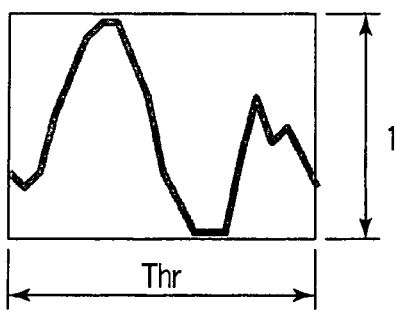
FIG. 23 is a graph showing an example of a diagnostic waveform obtained by CAB processing.

FIG. 22 is a graph showing an example of a reference waveform stored as a normal model for each age and each diagnosis region. This reference waveform has a period Tn normalized by a cardiac cycle and an amplitude An normalized by a standard velocity range. FIG. 23 shows an example of a diagnostic waveform obtained by CAB processing. Likewise, this diagnostic waveform is normalized by the cardiac cycle set by the cardiac cycle setting unit 63 and the standard velocity range.

Whether a diagnosis target region is normal or abnormal is determined by using this reference waveform and diagnostic waveform and a quality engineering technique. As the quality engineering technique, the MT (Mahalanobis-Taguchi) method, MTA (Mahalanobis-Taguchi Ajoint) method, MTS (Mahalanobis-Taguchi-Summit) method, or the like can be used.

Figure 24:
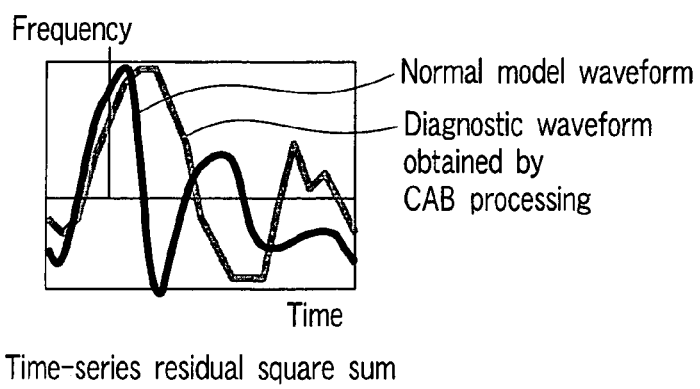
FIG. 24 is a graph for explaining a time-series residual square sum between a reference waveform and a diagnostic waveform.
Figure 25:
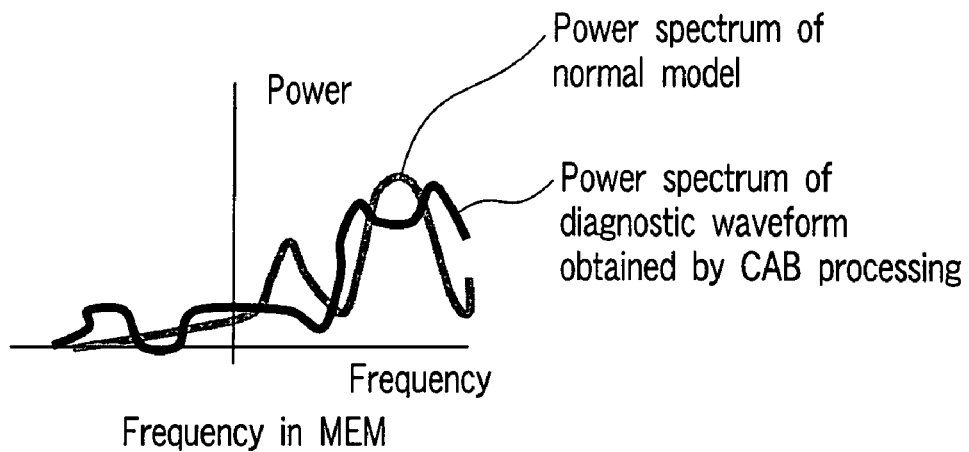
FIG. 25 is a graph for explaining the formation of a frequency spectrum by MEM.
Figure 26:
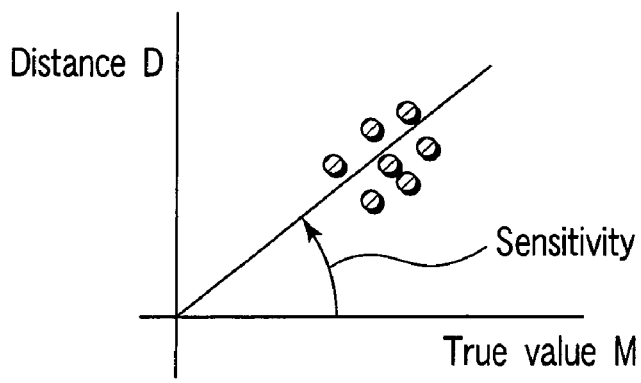
FIG. 26 is a graph for explaining evaluation by a quality optical technique using a residual square sum and frequency spectrum.

More specifically, as shown in FIG. 24, the analyzing unit 67 calculates the difference (residual) between the reference waveform (theoretical value) and the diagnostic waveform (actual value) at each time and the square sum of the residuals within a period Tn. As shown in FIG. 25, the analyzing unit 67 converts the time-series data of the reference waveform and diagnostic waveform into frequency spectra by MEM (Maximum Entropy Method). As shown in FIG. 26, the analyzing unit 67 further performs evaluation by using the MT method, MTA method, or MTS method using the calculated square sum of the residuals and frequency spectra. In this evaluation, if, for example, the square sum of the residuals exceeds a reference value, the analyzing unit 67 determines that the diagnosis target region is abnormal. If the square sum of the residuals is equal to or less than the reference value, the analyzing unit 67 determines that the diagnosis target region is normal.

The analyzing unit 67 determines whether a diagnosis target region is normal or abnormal by comparing the normal value (or the normal range) of each kind of measurement parameter stored in a diagnostic database like that shown in FIG. 27 with the diagnostic parameter measurement result obtained by the diagnostic parameter measuring function.

(Operation)

The operation of the ultrasonic Doppler diagnostic apparatus according to this embodiment will be described next.

Figure 28:
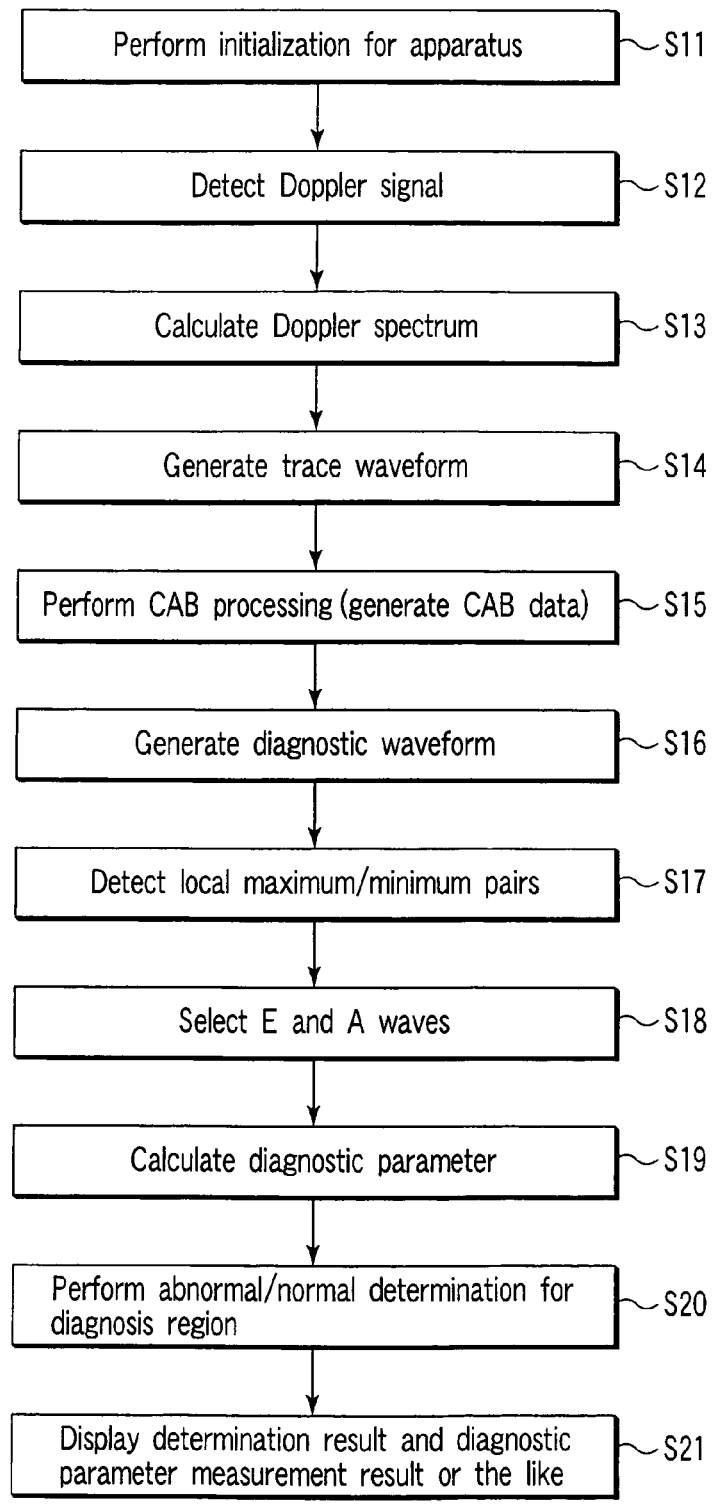
FIG. 28 is a flowchart showing the flow of processing executed by the ultrasonic Doppler diagnostic apparatus according to the second embodiment using a CAB function, a diagnostic parameter measuring function using CAB data, and a diagnosis support function using CAB data.

FIG. 28 is a flowchart showing the flow of processing executed by the ultrasonic Doppler diagnostic apparatus according to this embodiment using the CAB function, the diagnostic parameter measuring function using CAB data, and the diagnosis support function using CAB data.

First of all, initialization is performed for this ultrasonic Doppler diagnostic apparatus, a Doppler signal is detected in accordance with the initialization, and a Doppler spectrum is calculated (steps S11, S12, and S13). These processes are the same as those described in the first embodiment.

The trace waveform generating unit 61 generates a trace waveform Cp representing a temporal change in the maximum blood flow velocity Vp corresponding to a maximum frequency fp, and stores it in a data storage unit 5 (step S14). The feature amount selecting unit 64 executes the above CAB processing for the generated trace waveform Cp to generate CAB data (step S15). The feature amount selecting unit 64 performs statistical processing by using the CAB data obtained by the CAB processing to generate a diagnostic waveform (step S16).

The local maximum/minimum detecting unit 62 then detects local maximum/minimum pairs [p01, q01], [p02, q02], [p03, q03], ... by performing gradient operation and Laplacian operation for the generated diagnostic waveform (see FIG. 6A). The diagnostic waveform data to which these local maximum/minimum pairs are added is stored in the trace waveform storage area in the data storage unit 5 and supplied to the feature amount selecting unit 64 (step S17).

The feature amount selecting unit 64 sets one cardiac period T0 with respect to the diagnostic waveform on the basis of the cardiac cycle information set by the cardiac cycle setting unit 63. The feature amount selecting unit 64 selects E and A waves by applying a preset waveform selection criterion to a plurality of local maximum/minimum pairs added to the trace waveform in the cardiac period T0. The feature amount selecting unit 64 then supplies the position information of the selected E wave and the position information of the selected A wave to the diagnostic parameter measuring unit 65, together with the diagnostic waveform data (step S18).

The diagnostic parameter measuring unit 65 measures an amplitude VE of the E wave and an amplitude VA of the A wave of the diagnostic waveform on the basis of the position information of the E and A waves supplied from the feature amount selecting unit 64, and calculates the diagnostic parameter "E/A" in accordance with a ratio VE/VA. The diagnostic parameter measuring unit 65 further sets a tangent Ct with respect to a descending curve from the local maximum of the E wave, and calculates the interval between the position (time) of intersection between the tangent Ct and a baseline B1 and the position (time) of the E wave as a diagnostic parameter "DCT" (step S19). The diagnostic parameters "E/A" and "DCT" calculated in this manner are stored in a data storage unit 5.

The analyzing unit 67 executes analysis conforming to, e.g., the quality engineering technique by using a diagnostic waveform, reference waveform, and the like, and determines, on the basis of the analysis result, whether the diagnosis target region is normal (step S20).

The display unit 7 displays, on the monitor in a predetermined form, the B mode image data, the color Doppler image data, the Doppler spectrum data, the diagnostic waveform to which the information of the E and A waves is added, the measurement results on the diagnostic parameters "E/A" and "DCT", and the determination result indicating whether the diagnosis target region is normal or abnormal which are stored in the data storage unit 5 by the above sequence (step S21).

According to the above arrangement, the following effects can be obtained.

First of all, according to this ultrasonic diagnostic apparatus, a trace waveform can be extracted for each cardiac cycle in accordance with a time phase by CAB processing. The extracted trace waveforms for the respective cardiac cycles are arrayed along the time direction associated with a heart rate and the time direction in one heartbeat. The operator can therefore store a plurality of trace waveforms extracted for the respective heartbeats in a database, and can use it for quantitative analysis and the like. In addition, displaying the trace waveform extracted for each heartbeat in correspondence with a time phase makes it possible to visually check the trace waveform correspondence between heartbeats.

According to this ultrasonic diagnostic apparatus, a diagnostic waveform can be generated by performing statistical processing using CAB data obtained by CAB processing. Therefore, performing diagnostic parameter measurement by using this diagnostic waveform can reduce the influence of variations in Doppler waveform due to arrhythmia or the like.

According to this ultrasonic diagnostic apparatus, whether a diagnosis region is normal or abnormal can be determined on the basis of the diagnostic waveform obtained by statistical processing using CAB data, the diagnostic parameter measurement results obtained by using the diagnostic waveform, and presorted data associated with normal cases. In Doppler diagnosis, therefore, diagnosis support information with high objectivity based on CAB data can be provided, thereby contributing to an improvement in medical quality.

(Third Embodiment)

The third embodiment of the present invention will be described next. The ultrasonic Doppler diagnostic apparatus according to this embodiment has a function of rejecting or picking up an inappropriate event (e.g., an event which greatly differs from other events and is low in reliability) in statistical processing in the second embodiment.

Figure 29:
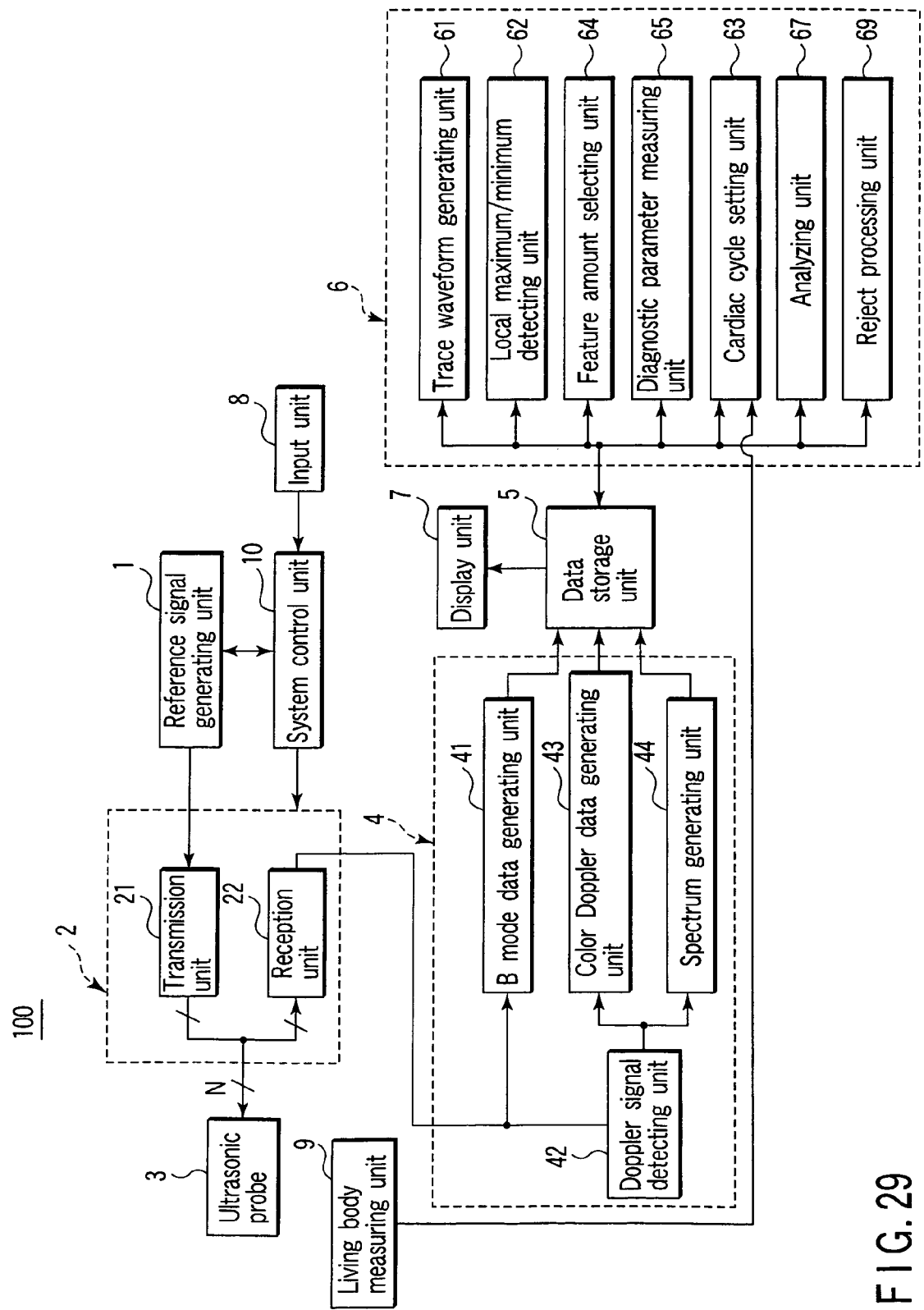
FIG. 29 is a block diagram showing the arrangement of an ultrasonic Doppler diagnostic apparatus according to the third embodiment.

FIG. 29 is a block diagram showing the arrangement of an ultrasonic Doppler diagnostic apparatus according to this embodiment. The ultrasonic Doppler diagnostic apparatus of this embodiment differs from that according to the second embodiment in that it further comprises a reject processing unit 69. The reject processing unit 69 executes processing (reject processing) conforming to the reject function to be described later.

(Reject Function)

The reject function of the ultrasonic Doppler diagnostic apparatus according to this embodiment will be described next. This function serves to remove a trace waveform with low reliability from a target for diagnostic parameter measurement processing using CAB data to stabilize the accuracy of diagnostic parameter measurement. This operation is equivalent to removing an event which falls outside a given threshold when an extracted trace waveform is set as a population, as shown in FIG. 30. This reject function includes a manual reject function and automatic reject function. A case wherein trace waveforms in the interval from the time immediately after freeze operation to the 10th heartbeat are set as diagnostic parameter measurement processing targets using CAB data will be described.

In the manual reject function, as shown in FIG. 31, first of all, trace waveforms corresponding to the 10 heartbeats are displayed as thumbnails by predetermined operation. The operator observes each trace waveform displayed as a thumbnail, and selects trace waveforms suitable for diagnostic parameter measurement processing using CAB data through an input unit 8. The selected trace waveforms are highlighted (the trace waveforms associated with the first, second, fourth, and sixth heartbeats in the case shown in FIG. 31), and the remaining trace waveforms are not used for diagnostic parameter measurement processing using CAB data (i.e., are rejected).

In the automatic reject function, for example, a PRD (Percent Root Mean Squire Difference) is calculated, and when the calculated value exceeds 10%, the corresponding trace waveform is determined as abnormal and automatically rejected from data inputs for statistical processing.

Figure 32:
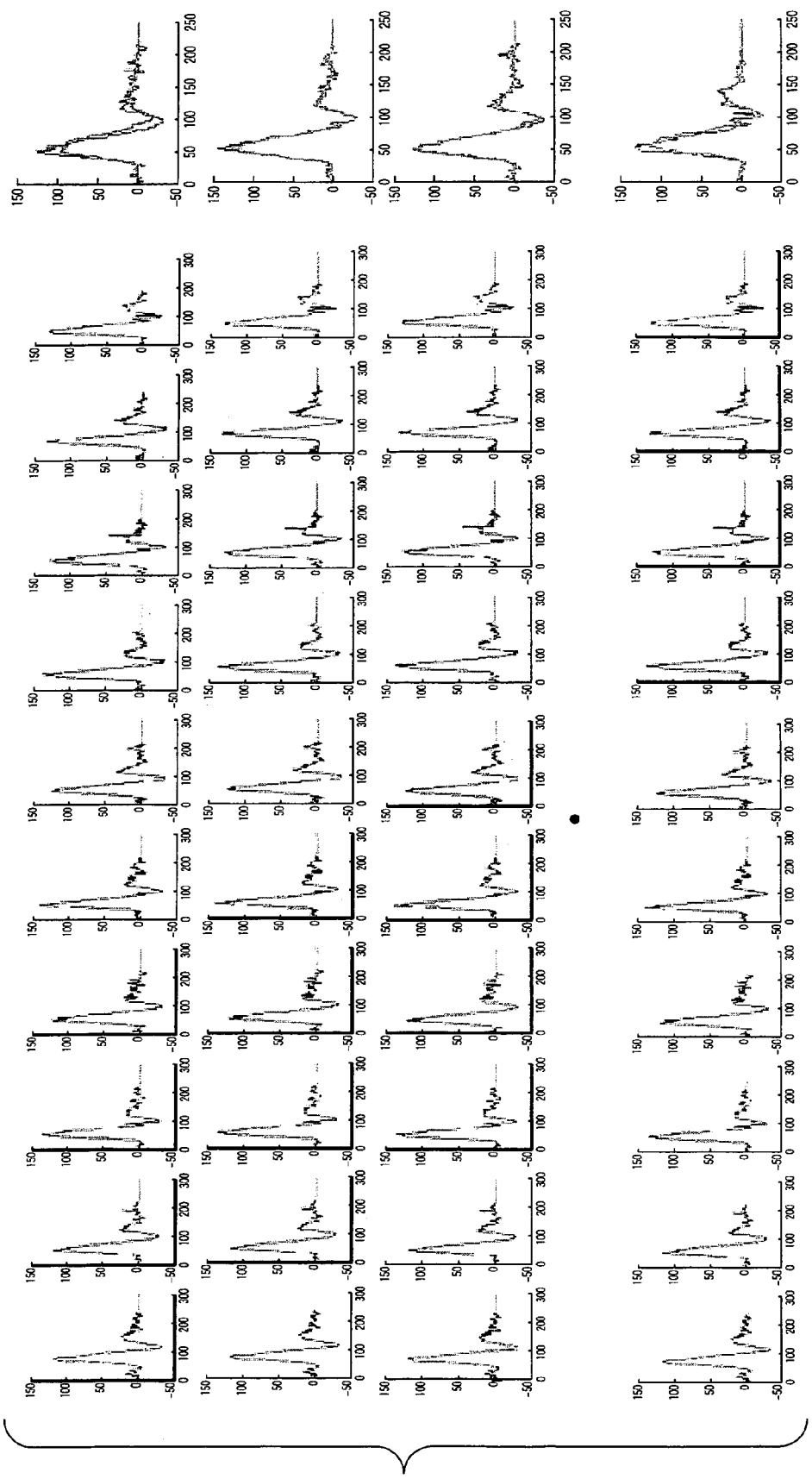
FIG. 32 is a graph for explaining an automatic reject function.
Figure 33:
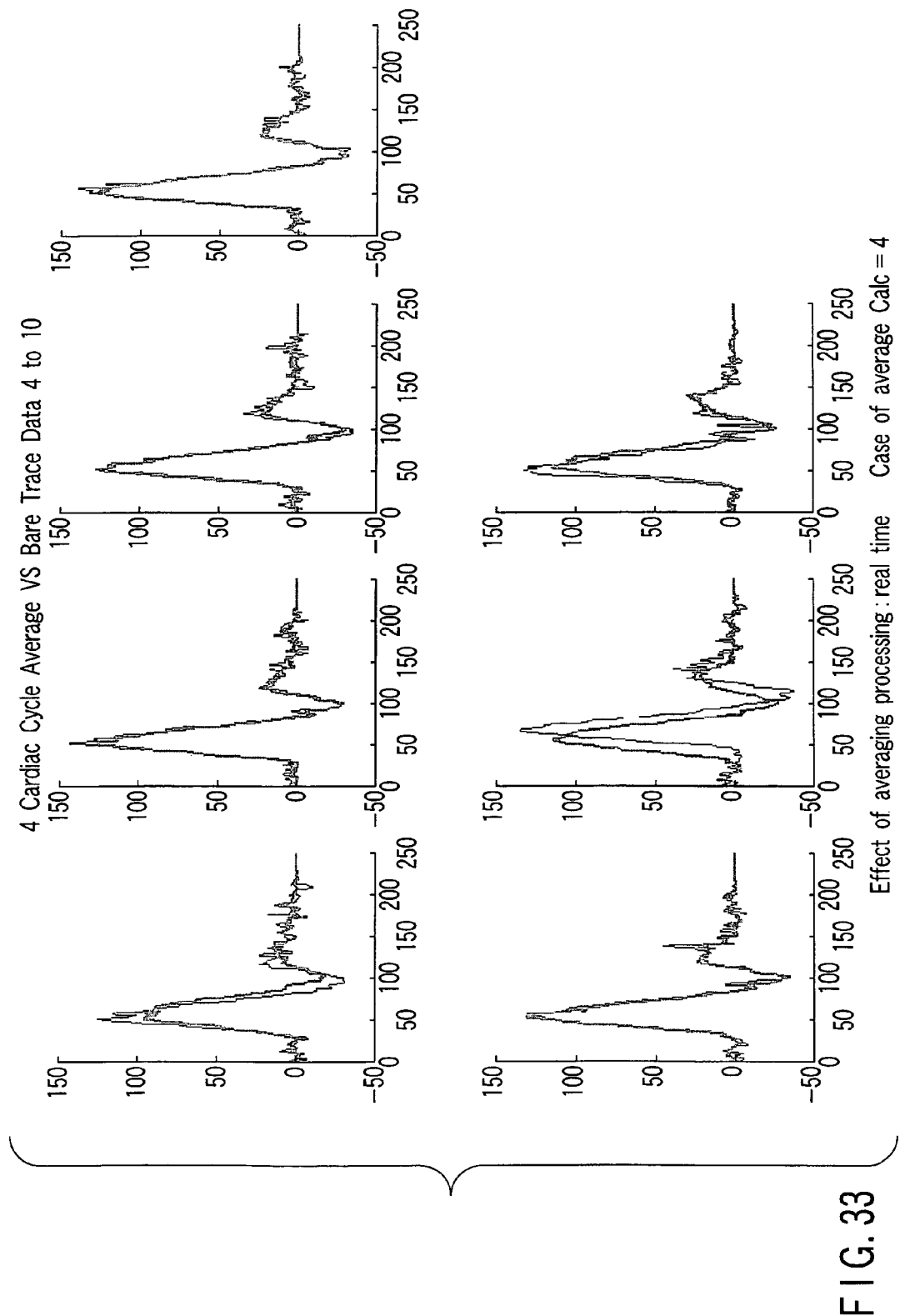
FIG. 33 is a graph for explaining the automatic reject function.

Another example of the automatic reject function serves to select a combination of a plurality of trace waveforms which CAB data contains and generate a diagnostic waveform for each combination. Therefore, trace waveforms which are excluded from the combination are automatically rejected. More specifically, a plurality of diagnostic waveforms are generated by shifting statistical processing one by one for every fourth heartbeat of continuous heartbeats starting from, for example, the seventh heartbeat after the stabilization of synchronous detection, as shown in FIG. 32. A diagnostic parameter measuring unit 65 uses the respective diagnostic waveforms to measure corresponding diagnostic parameters. In addition, for example, a plurality of diagnostic waveforms obtained by statistical processing are displayed as thumbnails, as shown in FIG. 33. At this stage, the operator can manually exclude a diagnostic waveform having a displacement from the displayed diagnostic waveforms. Referring to FIGS. 32 and 33, the thin lines represent trace waveforms having undergone no statistical processing, and the thick lines represent diagnostic waveforms obtained by statistical processing.

In addition, the manual reject function can be combined with the automatic reject function. For example, a threshold processing level is changed with respect to measurement parameters (e.g., a PS value, HR value, and the like) at each heartbeat in accordance with a reject threshold. Of changed waveforms, a waveform exceeding the threshold processing level is picked up as a reject target candidate and highlighted. The operator observes the highlighted reject target candidate, and executes statistical processing upon rejecting the candidate from the modulus of the population by the manual reject function.

Figure 34A:
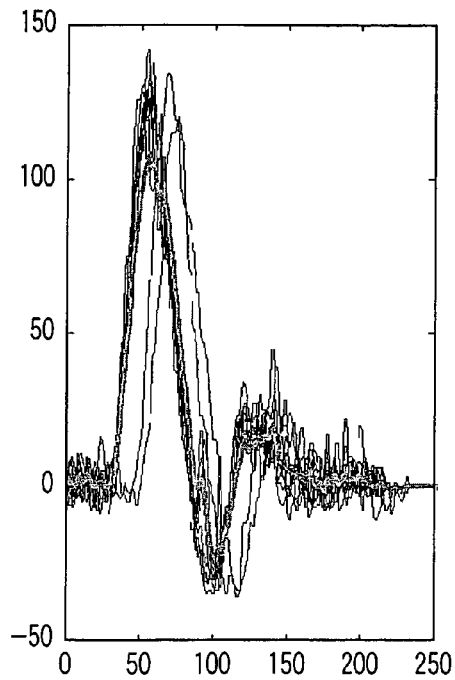
FIG. 34A is a graph showing a diagnostic waveform (thick line) obtained by statistical processing using heartbeats without reject processing.
Figure 34B:
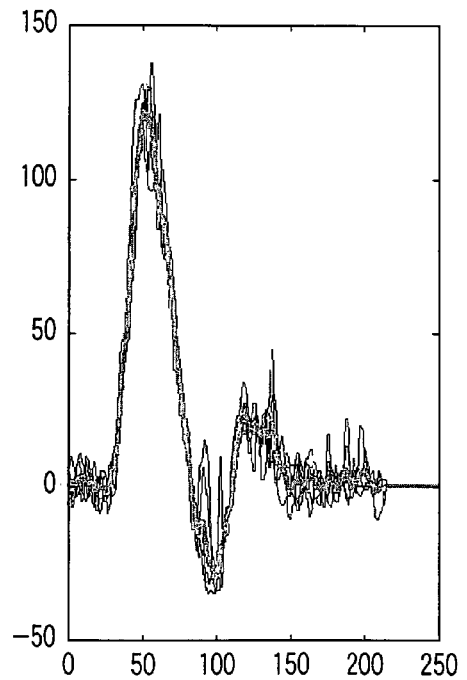
FIG. 34B is a graph showing a diagnostic waveform (thick line) obtained by statistical processing upon rejection of four heartbeats by reject processing.

FIG. 34A is a graph showing a diagnostic waveform (thick line) obtained by statistical processing using waveforms corresponding to 10 heartbeats without this reject processing. FIG. 34B is a graph showing a diagnostic waveform (thick line) obtained by statistical processing upon rejecting waveforms corresponding to four heartbeats from those corresponding to 10 heartbeats by the reject processing. It is obvious from the comparison between them that the diagnostic waveform obtained by reject processing is more approximate to each trace waveform used for this computation.

(Operation)

The operation of the ultrasonic Doppler diagnostic apparatus according to this embodiment will be described next.

FIG. 35 is a flowchart showing the flow of processing executed by this ultrasonic Doppler diagnostic apparatus using the reject function. Each process shown in FIG. 35 is executed in step S4 in FIG. 11.

First of all, initialization is performed for this ultrasonic Doppler diagnostic apparatus, a Doppler signal is detected in accordance with the initialization, and a Doppler spectrum is calculated (steps S31, S32, and S33). These processes are the same as those described in the first and second embodiments.

A trace waveform generating unit 61 generates a trace waveform Cp representing a temporal change in a maximum blood flow velocity Vp corresponding to a maximum frequency fp, and stores it in a data storage unit 5 (step S34). A feature amount selecting unit 64 executes the above CAB processing for the generated trace waveform Cp to generate CAB data (step S35). The reject processing unit 69 executes the above reject processing by using the trace waveforms for the respective heartbeats which constitute the generated CAB data (step S36). The feature amount selecting unit 64 generates a diagnostic waveform by performing statistical processing using the CAB data from which trace waveforms with low reliability are excepted by the reject processing (step S37).

Subsequently, as in the second embodiment, the processing from step S38 to step S42 is executed, and measurement results on diagnostic parameters "E/A" and "DCT" and a determination result indicating whether a diagnosis target region is normal or abnormal are displayed on the monitor in a predetermined form.

According to the above arrangement, the following effects can be obtained.

First of all, according to this ultrasonic diagnostic apparatus, trace waveforms with low reliability can be manually or automatically excepted from statistical processing targets using CAB data by the reject function. Therefore, a diagnostic waveform with high reliability can be generated. This makes it possible to realize high-quality diagnostic parameter measurement and diagnosis region abnormality/normality determination.

According to this ultrasonic diagnostic apparatus, trace waveforms with low reliability can be automatically picked up by the reject function. The operator can therefore improve the accuracy of statistical processing using CAB data by only individually discriminating each picked-up trace waveform with low reliability. This can reduce the workload on the operator in Doppler diagnosis.

The present invention is not limited to the above embodiments, and constituent elements can be modified and embodied in the execution stage within the spirit and scope of the invention.

(1) For example, in the first embodiment, the diagnostic parameters "E/A" and "DCT" effective for the measurement of a left ventricular blood inflow in the heart have been described. However, the present invention is not limited to this, and other diagnostic parameters may be used.

(2) It suffices to measure a pulmonary artery blood flow, left ventricular blood outflow, right ventricular blood inflow, a right ventricular blood outflow, or the like. As diagnostic parameters in pulmonary artery blood flow measurement, an S wave amplitude "VS", D wave amplitude "VD", and AD wave amplitude "VAD" are preferably measured.

FIG. 12B shows a trace waveform Cq of the maximum blood flow velocity Vp obtained by pulmonary artery blood flow measurement, and shows the positions (times) of the S, D, and AD waves selected on the basis of a selection criterion set when the ECG waveform Ec shown in FIG. 12A is used as a trigger waveform, and their amplitudes (flow velocities) VS, VD, and VAD.

FIG. 13 shows selection criteria in pulmonary artery blood flow measurement. These selection criteria are stored in advance as database data in the DB 2 in FIG. 7. That is, selection criteria for automatic selection of various kinds of waveforms on the basis of the cardiac cycles based on an ECG waveform, PCG waveform, and trace waveform and a selection criterion for automatic selection on the basis of a manually set cardiac cycle or heartbeat trigger are stored in the DB 2 stored in the storage circuit (not shown) of the feature amount selecting unit 64, like the selection criteria (see FIG. 8) in left ventricular blood inflow measurement.

Figure 14:
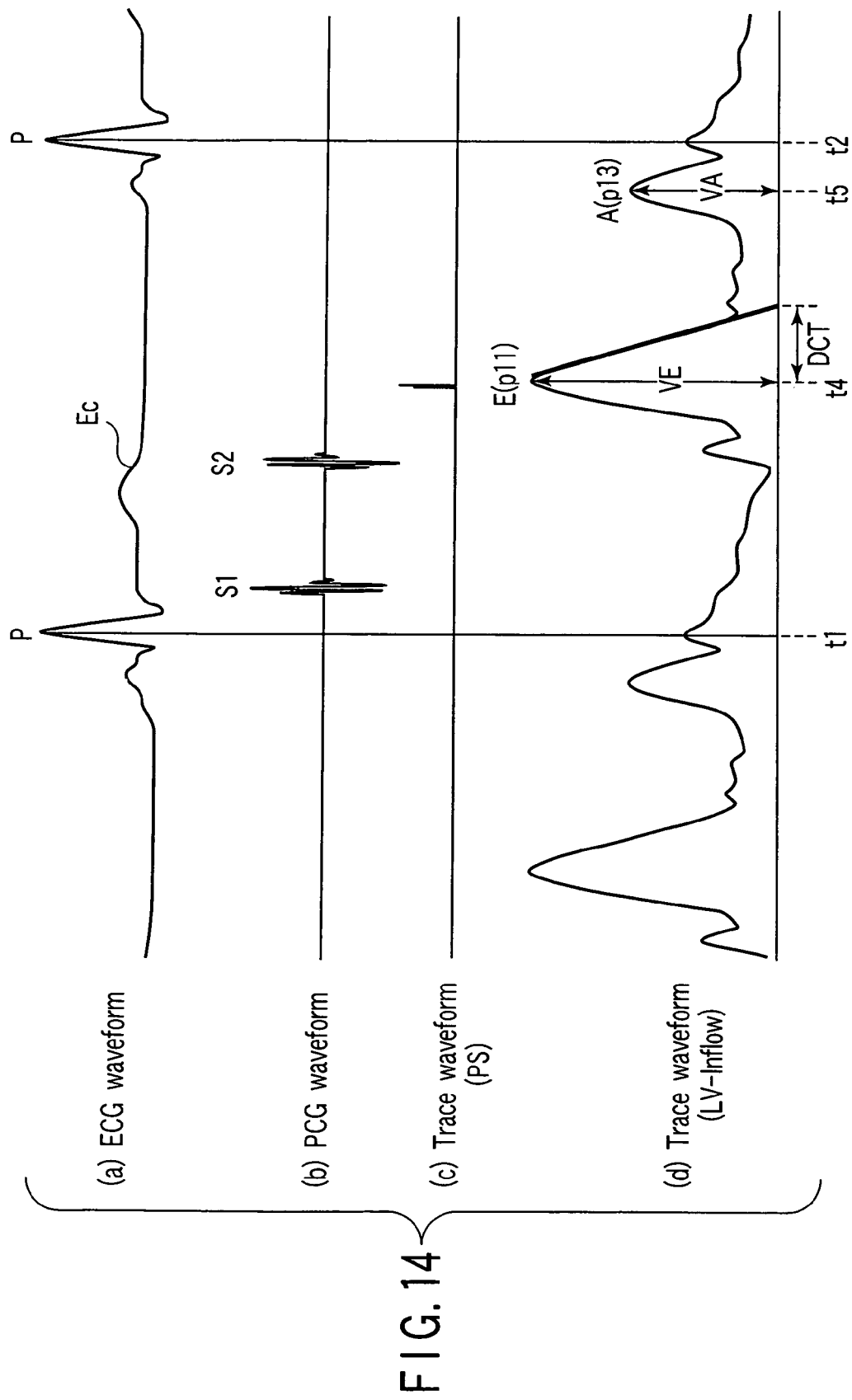
FIG. 14 is a graph showing trigger waveforms in a modification to the first embodiment.

(3) Each embodiment described above has exemplified the case wherein an ECG waveform is used as a trigger waveform. As has been described above with reference to FIGS. 8 and 13, waveform selection in a trace waveform may be performed on the basis of the heartbeat information of a PCG waveform or trace waveform. FIG. 14 shows a PCG waveform ("(b)" in FIG. 14) which can be used as a trigger waveform and a trigger signal ("(c)" in FIG. 14) based on a trace waveform, together with an ECG waveform ("(a)" in FIG. 14) and trace waveform ("(d)" in FIG. 14). The selection criteria set on the basis of trigger signals based on the PCG waveform and trace waveform are shown in FIGS. 8 and 13.

(4) Each embodiment described above has exemplified the case wherein diagnostic parameters are measured in real time with respect to a trace waveform displayed in real time together with B mode image data and color Doppler image data. However, such parameters may be automatically measured with respect to a frozen (still) trace waveform. In this case, diagnostic parameters can be automatically measured by selecting a trace waveform in a desired cardiac cycle upon scrolling a series of trace waveforms stored in a cine memory or the like in an arbitrary direction and applying the same procedure as that described above to the selected trace waveform.

(5) Each embodiment described above has exemplified the case wherein a trace waveform is generated on the basis of the maximum blood flow velocity Vp in a Doppler spectrum. However, the present invention is not limited to this, and a trace waveform may be generated on the basis of, for example, the average flow velocity Vc. In addition, although E and A waveforms and the like may be selected on the basis of local maximum/minimum pairs of a trace waveform as described above, the same effect can be obtained by selecting such waveforms on the basis of the magnitudes of local maximums.

(6) The transmission/reception unit 2 and ultrasonic probe 3 of the ultrasonic diagnostic apparatus 100 in each embodiment described above are not limited to those in the above embodiments. For example, a material other than a piezoelectric element may be used for a plurality of electroacoustic conversion elements provided for the ultrasonic probe 3. Alternatively, an ultrasonic probe having a two-dimensional array of such electroacoustic conversion elements may be used.

(7) Each embodiment described has exemplified the case wherein B mode image data and color Doppler image data are combined/displayed in the image data display area on the display unit 7. However, only one of the image data may be displayed.

(8) Each embodiment described above has exemplified the case wherein diagnostic parameter measurement is performed in real time by the ultrasonic Doppler diagnostic apparatus having the ultrasonic wave transmission/reception function. However, the present invention is not limited to this, and the above diagnostic parameter measurement may be performed by a medical workstation, personal computer, or the like using Doppler signal data acquired in the past.

Each function described in each embodiment can also be realized by installing programs corresponding to the respective processes in a computer and unarchiving them in a memory. In this case, the programs which can cause the computer to execute the corresponding techniques can be distributed by being stored in recording media such as magnetic disks (floppy (registered trademark) disks, hard disks, and the like), optical disks (CD-ROMs, DVDs, and the like), and semiconductor memories.

In addition, various inventions can be formed by proper combinations of a plurality of constituent elements disclosed in the above embodiments. For example, several constituent elements may be omitted from all the constituent elements disclosed in the above embodiments. Furthermore, constituent elements in the different embodiments may be properly combined.

What is claimed is:

1. An ultrasonic Doppler diagnostic apparatus comprising:
a Doppler signal detecting unit which detects a Doppler signal at a predetermined region from a reception signal obtained by performing ultrasonic wave transmission/reception with respect to an object to be examined;
a spectrum calculating unit which calculates a frequency spectrum of the Doppler signal;
a trace waveform generating unit which generates a trace waveform representing a temporal change in a predetermined spectrum component in the frequency spectrum;
a processing unit which generates data by extracting a trace waveform for each cardiac cycle from the generated trace waveform, and arraying said plurality of extracted trace waveforms along a first time axis representing a time direction associated with a heart rate and a second time axis representing a time direction within one cardiac cycle;
a statistical processing unit which generates a diagnostic waveform by performing statistical processing using the data;
a storage unit which stores a selection criterion;
a feature amount selecting unit which automatically selects a feature amount for the diagnostic waveform on the basis of the stored selection criterion;
a diagnostic parameter measuring unit which measures a diagnostic parameter on the basis of the feature amount; and
a display unit which displays a measurement result on the diagnostic parameter;
wherein the feature amount comprises an E wave and A wave of the trace waveform which are obtained in left ventricular blood inflow measurement; and
wherein the diagnostic parameter measuring unit measures at least one of an amplitude ratio E/A between E and A waves of a trace waveform of a maximum flow velocity and a lower limit period DCT of an E wave as the diagnostic parameter on the basis of the feature amount selected by the feature amount selecting unit.

2. An ultrasonic Doppler diagnostic apparatus according to claim 1, wherein the processing unit performs the extraction by using at least one of an electrocardiographic waveform and phonocardiographic waveform of the object.

3. An ultrasonic Doppler diagnostic apparatus according to claim 1, which further comprises a cardiac cycle setting unit which sets a cardiac cycle number, and in which
the processing unit performs the extraction by using the trace waveform containing the set cardiac cycle number.

4. An ultrasonic Doppler diagnostic apparatus according to claim 1, wherein the statistical processing is one of averaging processing associated with a plurality of heartbeats, Auto-Regressive time axis model calculation processing, and Auto-Regressive and exogenous time axis model calculation processing.

5. An ultrasonic Doppler diagnostic apparatus according to claim 1, which further comprises a reject processing unit which executes reject processing of excepting a trace waveform which does not meet a predetermined reference from trace waveforms in one cardiac cycle which constitute the data, and in which
the statistical processing unit executes the statistical processing by using the data for which the reject processing is executed.

6. An ultrasonic Doppler diagnostic apparatus according to claim 5, wherein
the display unit simultaneously displays said plurality of trace waveforms contained in the data, and the reject processing unit performs the reject processing so as to execute the statistical processing by using a trace waveform directly or indirectly selected by an operator from the displayed trace waveforms.

7. An ultrasonic Doppler diagnostic apparatus according to claim 5, wherein
the reject processing unit selects a plurality of combinations of the trace waveforms contained in the data, and
the statistical processing means generates a plurality of the diagnostic waveforms by executing the statistical processing for each of the combinations.

8. An ultrasonic Doppler diagnostic apparatus according to claim 1, wherein the trace waveform generating unit generates the trace waveform representing a temporal change in the predetermined spectrum component corresponding to a maximum blood flow velocity or average blood flow velocity at the predetermined region.

9. An ultrasonic Doppler diagnostic apparatus according to claim 1, which further comprises a local maximum/minimum detecting unit which detects a local maximum and minimum or a local maximum with respect to the trace waveform, and in which
the feature amount selecting unit selects the feature amount on the basis of a local maximum and minimum or a local maximum of a trace waveform in a predetermined cardiac cycle of the object.

10. An ultrasonic Doppler diagnostic apparatus according to claim 9, which further comprises a cardiac cycle setting unit which sets a cardiac cycle with respect to heartbeat information of the object, and in which
the feature amount selecting unit selects the feature amount on the basis of a local maximum and minimum or a local maximum of a trace waveform in the set predetermined cardiac cycle.

11. An ultrasonic Doppler diagnostic apparatus according to claim 10, wherein the cardiac cycle setting unit sets the predetermined cardiac cycle with respect to the trace waveform on the basis of at least one of an electrocardiographic waveform and phonocardiographic waveform of the object.

12. An ultrasonic Doppler diagnostic apparatus according to claim 10, wherein the display unit displays, in real time, a measurement result on the diagnostic parameter measured in a latest cardiac cycle of the trace waveform which is set by the cardiac cycle setting unit.

13. An ultrasonic Doppler diagnostic apparatus according to claim 1, which further comprises a storage unit which stores the trace waveform, and in which
the feature amount selecting unit selects the feature amount in a desired cardiac cycle of the trace waveform which is temporarily stored in the storage unit.

14. An ultrasonic Doppler diagnostic apparatus according to claim 1, wherein the selection criterion is stored as database data for each measurement target or each age group of objects.

15. An ultrasonic Doppler diagnostic apparatus according to claim 1, wherein the display unit displays the trace waveform and the measurement result on the diagnostic parameter in real time, and highlights a latest cardiac cycle of the trace waveform corresponding to the measurement result on the diagnostic parameter.

16. An ultrasonic Doppler diagnostic apparatus, comprising:
a Doppler signal detecting unit which detects a Doppler signal at a predetermined region from a reception signal obtained by performing ultrasonic wave transmission/reception with respect to an object to be examined;
a spectrum calculating unit which calculates a frequency spectrum of the Doppler signal;
a trace waveform generating unit which generates a trace waveform representing a temporal change in a predetermined spectrum component in the frequency spectrum;
a processing unit which generates data by extracting a trace waveform for each cardiac cycle from the generated trace waveform, and arraying said plurality of extracted trace waveforms along a first time axis representing a time direction associated with a heart rate and a second time axis representing a time direction within one cardiac cycle;
a statistical processing unit which generates a diagnostic waveform by performing statistical processing using the data;
a storage unit which stores a selection criterion;
a feature amount selecting unit which automatically selects a feature amount for the diagnostic waveform on the basis of the stored selection criterion;
a diagnostic parameter measuring unit which measures a diagnostic parameter on the basis of the feature amount; and
a display unit which displays a measurement result on the diagnostic parameter;
wherein the feature amount comprises at least one of S, D, and AD waves of the trace waveform which are obtained in pulmonary artery blood flow measurement.

17. An ultrasonic Doppler diagnostic apparatus according to claim 16, wherein the diagnostic parameter measuring unit measures, as a diagnostic parameter, at least one of a velocity VS of an S wave in pulmonary artery blood flow measurement, a velocity VD of a D wave in pulmonary artery blood flow measurement, and a velocity VAD of an AR wave in pulmonary artery blood flow measurement on the basis of the feature amount selected by the feature amount selecting unit.

18. An ultrasonic Doppler diagnostic apparatus comprising:
a Doppler signal detecting unit which detects a Doppler signal at a predetermined region from a reception signal obtained by performing ultrasonic wave transmission/reception with respect to an object to be examined;
a spectrum calculating unit which calculates a frequency spectrum of the Doppler signal;
a trace waveform generating unit which generates a trace waveform representing a temporal change in a predetermined spectrum component in the frequency spectrum;
a storage unit which stores a selection criterion;
a feature amount selecting unit which automatically selects a feature amount with respect to the trace waveform in a predetermined cardiac cycle of the object on the basis of the stored selection criterion;
a diagnostic parameter measuring unit which measures a diagnostic parameter on the basis of the feature amount; and
a display unit which displays a measurement result on the diagnostic parameter;
wherein the feature amount comprises an E wave and A wave of the trace waveform which are obtained in left ventricular blood inflow measurement; and
wherein the diagnostic parameter measuring unit measures at least one of an amplitude ratio E/A between E and A waves of a trace waveform of a maximum flow velocity and a lower limit period DCT of an E wave as the diagnostic parameter on the basis of the feature amount selected by the feature amount selecting unit.

19. An ultrasonic Doppler diagnostic apparatus according to claim 18, wherein the trace waveform generating unit generates the trace waveform representing a temporal change in the predetermined spectrum component corresponding to a maximum blood flow velocity or average blood flow velocity at the predetermined region.

20. An ultrasonic Doppler diagnostic apparatus according to claim 18, which further comprises a local maximum/minimum detecting unit which detects a local maximum and minimum or a local maximum with respect to the trace waveform, and in which the feature amount selecting unit selects the feature amount on the basis of a local maximum and minimum or a local maximum of a trace waveform in a predetermined cardiac cycle of the object.

21. An ultrasonic Doppler diagnostic apparatus according to claim 20, which further comprises a cardiac cycle setting unit which sets a cardiac cycle with respect to heartbeat information of the object, and in which the feature amount selecting unit selects the feature amount on the basis of a local maximum and minimum or a local maximum of a trace waveform in the set predetermined cardiac cycle.

22. An ultrasonic Doppler diagnostic apparatus according to claim 21, wherein the cardiac cycle setting unit sets the predetermined cardiac cycle with respect to the trace waveform on the basis of at least one of an electrocardiographic waveform and phonocardiographic waveform of the object.

23. An ultrasonic Doppler diagnostic apparatus according to claim 21, wherein the display unit displays, in real time, a measurement result on the diagnostic parameter measured in a latest cardiac cycle of the trace waveform which is set by the cardiac cycle setting unit.

24. An ultrasonic Doppler diagnostic apparatus according to claim 18, which further comprises a storage unit which stores the trace waveform, and in which the feature amount selecting unit selects the feature amount in a desired cardiac cycle of the trace waveform which is temporarily stored in the storage unit.

25. An ultrasonic Doppler diagnostic apparatus according to claim 18, wherein the selection criterion is stored as database data for each measurement target or each age group of objects.

26. An ultrasonic Doppler diagnostic apparatus according to claim 18, wherein the display unit displays the trace waveform and the measurement result on the diagnostic parameter in real time, and highlights a latest cardiac cycle of the trace waveform corresponding to the measurement result on the diagnostic parameter.

27. An ultrasonic Doppler diagnostic apparatus comprising:
a Doppler signal detecting unit which detects a Doppler signal at a predetermined region from a reception signal obtained by performing ultrasonic wave transmission/reception with respect to an object to be examined;
a spectrum calculating unit which calculates a frequency spectrum of the Doppler signal;
a trace waveform generating unit which generates a trace waveform representing a temporal change in a predetermined spectrum component in the frequency spectrum;
a storage unit which stores a selection criterion;
a feature amount selecting unit which automatically selects a feature amount with respect to the trace waveform in a predetermined cardiac cycle of the object on the basis of the stored selection criterion;
a diagnostic parameter measuring unit which measures a diagnostic parameter on the basis of the feature amount; and
a display unit which displays a measurement result on the diagnostic parameter;
wherein the feature amount comprises at least one of S, D, and AD waves of the trace waveform which are obtained in pulmonary artery blood flow measurement.

28. An ultrasonic Doppler diagnostic apparatus according to claim 27, wherein the diagnostic parameter measuring unit measures, as a diagnostic parameter, at least one of a velocity VS of an S wave in pulmonary artery blood flow measurement, a velocity VD of a D wave in pulmonary artery blood flow measurement, and a velocity VAD of an AR wave in pulmonary artery blood flow measurement on the basis of the feature amount selected by the feature amount selecting unit.

29. A measuring method of diagnostic parameter comprising:
detecting a Doppler signal at a predetermined region from a reception signal obtained by performing ultrasonic wave transmission/reception with respect to an object to be examined;
calculating a frequency spectrum of the Doppler signal;
generating a trace waveform representing a temporal change in a predetermined spectrum component in the frequency spectrum;
generating data by extracting a trace waveform for each cardiac cycle from the generated trace waveform, and arraying said plurality of extracted trace waveforms along a first time axis representing a time direction associated with a heart rate and a second time axis representing a time direction within one cardiac cycle;
generating a diagnostic waveform by performing statistical processing using the data;
automatically selecting a feature amount with respect to the diagnostic waveform on the basis of a stored selection criterion;
measuring a diagnostic parameter on the basis of the feature amount; and
displaying a measurement result on the diagnostic parameter;
wherein the feature amount comprises an E wave and A wave of the trace waveform which are obtained in left ventricular blood inflow measurement; and
wherein the measuring a diagnostic parameter measures at least one of an amplitude ratio E/A between E and A waves of a trace waveform of a maximum flow velocity and a lower limit period DCT of an E wave as the diagnostic parameter on the basis of the automatically selecting a feature amount.

30. A measuring method of diagnostic parameter comprising:
detecting a Doppler signal at a predetermined region from a reception signal obtained by performing ultrasonic wave transmission/reception with respect to an object to be examined;
calculating a frequency spectrum of the Doppler signal;
generating a trace waveform representing a temporal change in a predetermined spectrum component in the frequency spectrum;
automatically selecting a feature amount with respect to the trace waveform in a predetermined cardiac cycle of the object on the basis of a stored selection criterion;
measuring a diagnostic parameter on the basis of the feature amount; and
displaying a measurement result on the diagnostic parameter;
wherein the feature amount comprises an E wave and A wave of the trace waveform which are obtained in left ventricular blood inflow measurement; and
wherein the measuring a diagnostic parameter measures at least one of an amplitude ratio E/A between E and A waves of a trace waveform of a maximum flow velocity and a lower limit period DCT of an E wave as the diagnostic parameter on the basis of the automatically selecting a feature amount.

* * * * *